(12) United States Patent
Wang

(10) Patent No.: US 7,985,836 B2
(45) Date of Patent: *Jul. 26, 2011

(54) ANTIMICROBIAL PEPTIDES AND METHODS OF IDENTIFYING THE SAME

(75) Inventor: Guangshun Wang, Omaha, NE (US)

(73) Assignee: Board of Regents of the University of Nebraska, Omaha, NE (US)

( * ) Notice: Subject to any disclaimer, the term of this patent is extended or adjusted under 35 U.S.C. 154(b) by 156 days.

This patent is subject to a terminal disclaimer.

(21) Appl. No.: 12/334,966

(22) Filed: Dec. 15, 2008

(65) Prior Publication Data

US 2009/0156499 A1 Jun. 18, 2009

Related U.S. Application Data

(62) Division of application No. 11/586,943, filed on Oct. 26, 2006, now Pat. No. 7,465,784.

(51) Int. Cl.
*A61K 38/00* (2006.01)
*A61K 38/04* (2006.01)
*A61K 51/00* (2006.01)

(52) U.S. Cl. ......... 530/327; 530/326; 514/1.1; 424/1.69

(58) Field of Classification Search .................. None
See application file for complete search history.

(56) References Cited

U.S. PATENT DOCUMENTS

| 4,683,195 A | 7/1987 | Mullis |
| 4,965,188 A | 10/1990 | Mullis |
| 2006/0223755 A1 | 10/2006 | Grote |

FOREIGN PATENT DOCUMENTS

| WO | 2004058798 | | 7/2004 |
| WO | WO 2004058798 | * | 7/2004 |
| WO | 2004/067563 | | 8/2004 |
| WO | 2007/148078 | | 12/2007 |

OTHER PUBLICATIONS

Papo et al.; 2004; "Effect of drastic sequence alteration and d-amino acid incorporation on the membrane binding behavior of lytic peptides," Biochemistry; 43:6393-6403.
Piotto et al.; 1992; "Gradient-tailored excitation for single-quantum NMR spectroscopy of aqueous solutions," J. Biomol. NMR; 2:661-665.
Porcelli et al.; Oct. 29, 2004; "Structure and orientation of parsdaxin determined by NMR experiments in model membranes," J. Biol. Chem.; 279:45815-45823.
Powers et al.; 2005; "Solution structure and interaction of the antimicrobial polyphemusins with lipid membranes," Biochemistry; 44:15504-15513.
Putsep et al.; Oct. 12, 2002; "Deficiency of antibacterial peptides in patients with morbus Kostmann: an observation study," Lancet; 360:1144-1149.
Rance et al.; Dec. 16, 1983; "Improved spectral resolution in COSY 1H NMR spectra of proteins via double quantum filtering," Biochem. Biophys. Res. Commun.; 117:479-485.
Rosenfeld et al.; Jan. 20, 2006 (published, papers in press, Nov. 17, 2005); "Endotoxin (lipopolysaccharide) neutralization by innate immunity host-defense peptides," J. Biol. Chem.; 281:1636-1643.
Rozek et al.; 2000; "The antibiotic and anticancer active aurein peptides from the Australian bell frogs *Litoria aurea* and *Litoria raniformis*," Eur. J. Biochem.; 267:5330-5341.
Schwieters, C.D., et al., "The Xplor-NIH NMR molecular structure determination package," J. Magnetic Resonance, 160:65-73 (2003).
Shai et al.; Mar. 29, 1996; "Diastereomers of cytolysins, a novel class of potent antibacterial peptides," J. Biol. Chem.; 271:7305-7308.
Sigurdardottir, T. et al.; 2006, "In Siulico Identification and Biological Evaluation of Antimicrobial Peptides Based on Human Cathelicidin LL-37;" Antimicrobial Agents and Chemotherapy, vol. 50, No. 9, p. 2983-2989.
Sorenson et al.; Oct. 1, 1997; "The human antibacterial cathelicidin, hCAP-18, is synthesized in myelocytes and metamyelocytes and localized to specific granules in neutrophils," Blood; 90:2796-2803.
Spera et al.; 1991; "Empirical correlation between protein backbone conformation and Calpha and Cbeta 13C nuclear magentic resonance chemical shifts," J. Am. Chem. Soc.; 113:5490-5492.
Tjabringa et al.; 2003; "The antimicrobial peptide LL-37 activates innate immunity at the airway epithelial surface by transactivation of the epidermal growth factor receptor," J. Immunol.; 171:6690-6696.
Wang et al.; 1996; "Conformations of human apolipoprotein E(263-286) and E(267-289) in aqueous solutions of sodium dodecyl sulfate by CD and 1H NMR," J. Biochemistry; 35:10358-10366.
Wang et al.; 1996; "Conformation of human serum apolipoprotein A-I(166-185) in the presence of sodium dodecyl sulfate or dodecylphosphocholine by 1H-NMR and CD. Evidence for specific peptide-SDS interactions," Biochimica et Biophysica Acta; 1301:174-184.
Wang et al.; 1997; "The helix-hinge-helix structural motif in human apolipoprotein A-I determined by NMR spectrocopy," J. Biochemistry; 36:13657-13666.
Wang et al.; Dec. 22, 2000; "A novel membrane anchor function for the N-terminal amphipathic sequence of the signal-transducing protein IIAglucose of the *Escherichia coli* phosphotransferase system," J. Biol. Chem.; 275:39811-39814.
Wang et al.; Jun. 2, 2000; "A common interface on histidine-containing phosphocarrier protein for interaction with its partner proteins," J. Biol. Chem.; 275:16401-16403.
Wang, G.; 2002; "How the lipid-free structure of the N-terminal truncated human apoA-I converts to the lipid-bound form: new insights from NMR and X-ray structural comparison," FEBS Lett.; 529:157-161.
Wang et al.; 2003; "Solution structure of the N-terminal amphitropic domain of *Escherichia coli* glucose-specific enzyme IIA in membrane-mimetic micelles," Protein Sci.; 12:1087-1096 and 1 cover sheet.

(Continued)

*Primary Examiner* — Maury Audet

(74) *Attorney, Agent, or Firm* — Dann Dorfman Herrell & Skillman; Robert C. Netter, Jr.

(57) ABSTRACT

Antimicrobial peptides and methods of identifying the same are provided.

10 Claims, 14 Drawing Sheets

OTHER PUBLICATIONS

Figure 1:
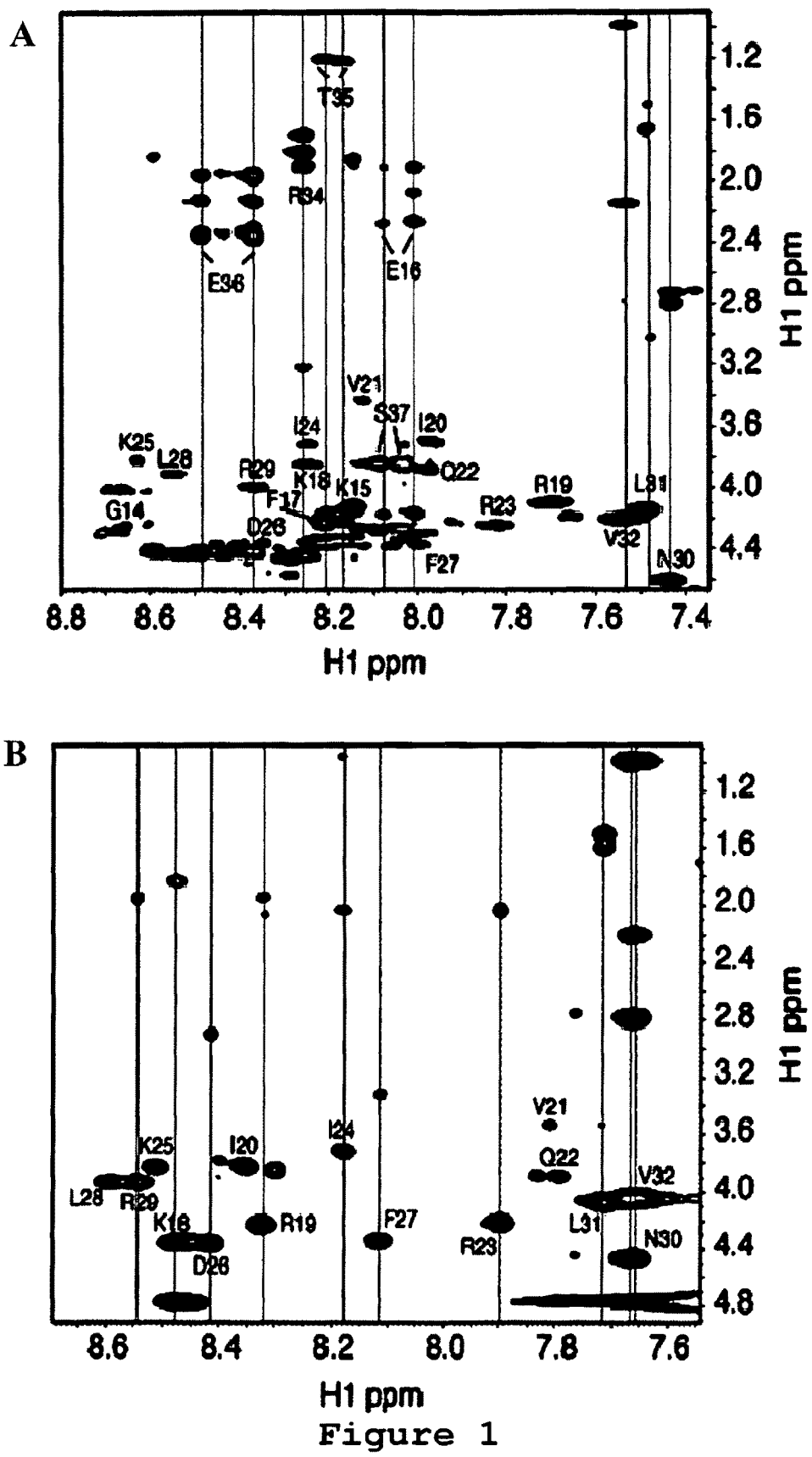

Wang, G., et al., "Short-chain diacyl phosphatidylglycerols: which one to choose for the NMR structural determination of a membrane-associated peptide from *Escherichia coli*?" Spectroscopy, 18:257-264, (2004).

Wang et al., 2004; "APD: the antimicrobial peptide database," Nucleic Acids Res.; 32:D590-D592.

Wang et al.; Feb. 18, 2005; "Correlation of three-dimensional structures with the antibacterial activity of a group of peptides designed based on a nontoxic bacterial membrane anchor," J. Biol. Chem.; 280:5803-5811.

Wang, G., "Structural biology of antimicrobial peptides by NMR spectroscopy," Current Organic Chemistry, 10 (5):569-581, (2006).

Wishart et al.; 1991; "Relationship between nuclear magnetic resonance chemical shift and protein secondary structure," J. Mol. Biol.; 222:311-333.

Yu et al.; 2002; "Solution structure of a cathelicidin-derived antimicrobial peptide, CRAMP as determined by NMR spectroscopy," J. Pept. Res.; 60:1-9.

Zanetti, M., "Cathelicidins, multifunctional peptides of the innate immunity," J. Leukoc. Biol., 75:39-48, (2004).

Zasloff, M.; 2002; "Antimicrobial peptides of multicellular organisms," Nature; 415:389-395.

Zhang et al.; 2003; "Binding of peptides with basic and aromatic residues to bilayer membranes," J. Biol. Chem.; 278:21459-21466.

Agerberth et al.; Nov. 1, 2000; "The human antimicrobial and chemotactic peptides LL-37 and alpha-defensins are expressed by specific lymphocyte and monocyte populations," Blood; 96(9):3086-3093.

Allen et al.; 2003; "Structure of gramicidin A in a lipid bilayer environment determined using molecular dynamics simulations and solid-state NMR data," J. Am. Chem. Soc.; 125:9868-9877.

Bax et al.; 1985; "MLEV-17-based two-dimensional homonuclear magnetization transfer spectroscopy," J. Magn. Reson.; 65:355-360.

Bechinger, B., "Detergent-like properties of magainin antibiotic peptides: A 31P solid-state NMR spectroscopy study," Biochimica et Biophysica Acta, 1712:101-108, (2005).

Bowdish et al.; 2004; "The human cationic peptide LL-37 induces activation of the extracellular signal-regulated kinase and p38 kinase pathways in primary human monocytes," J. Immunol.; 172:3758-3765.

Braff et al.; 2005; "Structure-function relationships among human cathelicidin peptides: dissociation of antimicrobial properties from host immunostimulatory activities," J. Immunol.; 174:4271-4278.

Brahmachary et al.; 2004; "ANTIMIC: a database of antimicrobial sequences," Nucleic Acids Res.; 32:D586-589.

Burley et al.; 1985; "Aromatic-aromatic interaction: a mechanism of protein structure stabilization," Science; 229:23-28 and one sheet of abstract.

Chen et al.; Apr. 1, 2005; "Rational design of alpha-helical antimicrobial peptides with enhanced activities and specificicty/therapeutic index," J. Biol. Chem.; 280:12316-12329.

Clore et al.; 1998; "Determining the structures of large proteins and protein complexes by NMR," Trends Biotechnol. 16:22-34.

Cornilescu et al.; 1999; "Protein backbone angle restraints from searching a database for chemical shift and sequence homology," J. Biomol. NMR; 13:289-302.

Delaglio et al.; 1995; "NMRPipe: a mutlidimensional spectral processing system based on UNIX pipes," J. Biomol. NMR; 6:277-293.

Di Nardo et al.; 2003; "Cutting edge: mast cell antimicrobial activity is mediated by expression of cathelicidin antimicrobial peptide," J. Immunol.; 170:2274-2278.

Dorschner et.al.; 2001; "Cutaneous injury induces the release of cathelicidin anti-microbial peptides active against group A Steptococcus," Invest. Dermatol.; 117:91-97.

Frohm et al.; Jun. 13, 1997; "The expression of the gene coding for the antibacterial peptide LL-37 is induced in human keratinocytes during inflammatory disorders," J. Biol.Chem.; 272:15258-15263.

Garrett et al.; 1991; "A common sense approach to peak picking in two-, three-, and four-dimensional spectra using automatic computer analysis of contour diagrams," J. Magn. Reson.; 95:214-220.

Griesinger et al.; 1988; "Clean TOCSY for 1H spin system identification in macromolecules," J. Am. Chem. Soc.; 110:7870-7872.

Gudmundsson et al.; 1996; "The human gene FALL39 and processing of the cathelin precursor to the antibacterial peptide LL-37 in granulocytes," Eur. J. Biochem.; 238:325-332.

Hallock et al.; Aug. 2002; "Membrane composition determines pardaxin's mechanism of lipid bilayer disruption," Biophys. J.; 83:1004-1013.

Hansen et al.; 1989; "Re-examination and further development of a precise and rapid dye method for measuring cell growth/cell kill," J. Immunol. Methods; 199:203-210.

Henry et al.; 1994; "Methods to study membrane protein structure in solution," Methods Enzymol.; 239:515-535.

Henzler-Wildman et al.; 2003; "Mechanism of lipid bilayer disruption by the human antimicrobial peptide, LL-37," Biochemistry; 42:6545-6558.

Henzler-Wildman et al.; 2004; "Peturbation of the hydrophobic core of lipid bilayers by the human antimicrobial peptide LL-37," Biochemistry; 43:8459-8469.

Jeener et al.; Dec. 1979; "Investigation of exchange processes by two-dimensional NMR spectroscopy," J. Chem. Phys.; 71:4546-4553.

Johansson et al.; Feb. 6, 1998; "Conformation-dependent antibacteiral activity of the naturally occurring human peptide LL-37," J. Biol. Chem.; 273:3718-3724.

Kay et al.; 1992; "Pure absorption gradient enhanced heteronuclear single quantum correlation spectroscopy with improved sensitivity," J. Am Chem. Soc.; 114:10663-10665.

Keifer et al.; 2004; "Effects of detergent alkyl chain length and chemical structure on the properties of a micelle-bound bacterial membrane targeting peptide," Anal. Biochem.; 331:33-39.

Kim et al.; 2005; "Correlation between the activities of alpha-helical antimicrobial peptides and hydrophobicities represented as RP HPLC retention times," J. Peptides; 26:2050-2056.

Koradi, R., et al., "MOLMOL: a program for display and analysis of macromolecular structures," J. Mol. Graphics 14:51-55, (1996).

Laskowski, R.A., et al., "Procheck: a program to check the stereochemical quality of protein structures," J. Appl. Cryst., 26:283-291, (1993).

Lee et al.; Mar. 8, 2005; "Expression of an additional cathelcidin antimicrobial peptide protects against bacterial skin infection," Proc. Natl. Acad. Sci. U.S.A.; 102:3750-3755.

Li et al.; 2006; "Cloning, expression, isotope labeling, and purification of human antimicrobial peptide LL-37 in *Escherichia coli* for NMR studies," Protein Exp. Purif.; 47:498-505.

Li et al.; 2006; "Solution structures of human LL-37 fragments and NMR-based identification of a minimal membrane-targeting antimicrobial and anticancer region," J. Am. Chem. Soc.; 128:5776-5785.

Li, X. et al.; 2006; "NMR Studies of Aurein 1.2 Analogs," Biochimica et Biophysica Acta; BBAMEM-79074; p. 12; 4C; 5, 7.

Sieprawska-Lupa et al.; 2004; "Degradation of human antimicrobial peptide LL-37 by *Staphylococcus aureus*-derived proteinases," Antimicrob. Agents Chemother.; 48:4673-4679.

Mani, R., et al., "Membrane-disruptive abilities of beta-hairpin antimicrobial peptides correlate with conformation and activity: A 31P and 1H NMR study," Biochimica et Biophysica Acta, 1716:11-18, (2005).

Mark, K.S., et al., "Increased permeability of primary cultured brain microvessel endothelial cell monolayers following TNF-alpha exposure," Life Sci., 64(21):1941-1953, (1999).

Markley et al.; 1998; "Recommendations for the presentation of NMR structures of proteins and nucleic acids," J. Biomol. NMR; 12:1-23.

McPhee et al.; 2005 (published online Aug. 15, 2005); "Function and therapeutic potential of host defence peptides," J. Pept. Sci., 11:677-687.

Mecke et al.; Dec. 2005; "Membrane thinning due to antimicrobial peptide binding: an atomic force microscopy study of MSI-78 in lipid bilayers," Biophys. J.; 89:4043-4050.

Mitchell et al.; 2003; "D-amino acid residues in peptides and proteins," Proteins; 50:563-571.

Murakami et al.; 2004; "Postsecretory processing generates multiple cathelicidins for enhanced topical antimicrobial defense," J. Immunol.; 172:3070-3077.

Mygind et al.; Oct. 13, 2005; "Plectasin is a peptide antibiotic with therapeutic potential from a saprophytic fungus," Nature; 437:975-980.

Nagaoka et al.; 2002; "Augmentation of the lipopolysaccharide-neutralizing activities of human cathelicidin CAP18/fLL-37-derived antimicrobial peptides by replacement with hydrophobic and cationic amino acid residues," Clin. Diagn. Lab Immunol.; 9:972-982.

Nell et al.; 2006; "Development of novel LL-37 derived antimicrobial peptides with LPS adn LTA neutralizing and antimicrobial activities for therapeutic application," Peptides; 27:649-660.

Nizet et al.; Nov. 22, 2001; "Innate antimicrobial peptide protects the skin from invasive bacterial infection," Nature; 414:454-457.

Opella et al.; 2004; "Structure determination of membrane proteins by NMR spectroscopy," Chem. Rev.; 104:3587-3606.

Oren et al.; 1997; "Selective lysis of bacteria but not mammalian cells by diastereomers of melittin: structure-function study," Biochemistry; 36:1826-1835.

Oren et al.; 1999; "Structure and organization of the human antimicrobial peptide LL-37 in phospholipid membranes: relevance to the molecular basis for its non-cell-selective activity," Biochem. J.; 341:501-513.

Oren et al.; 2002; "Structures and mode of membrane interaction of a short alpha helical lytic peptide and its diastereomer determined by NMR, FTIR, and fluorescence spectroscopy," Eur. J. Biochem.; 269:3869-3880.

\* cited by examiner

SEQUENCE LISTING

<160> NUMBER OF SEQ ID NOS: 20

<210> SEQ ID NO 1
<211> LENGTH: 37
<212> TYPE: PRT
<213> ORGANISM: Artificial Sequence
<220> FEATURE:
<223> OTHER INFORMATION: Synthetic Sequence

<400> SEQUENCE: 1

Leu Leu Gly Asp Phe Phe Arg Lys Ser Lys Glu Lys Ile Gly Lys Glu
1               5                   10                  15

```
Phe Lys Arg Ile Val Gln Arg Ile Lys Asp Phe Leu Arg Asn Leu Val
            20                  25                  30

Pro Arg Thr Glu Ser
        35

<210> SEQ ID NO 2
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 2

Leu Leu Gly Asp Phe Phe Arg Lys Ser Lys Glu Lys
1               5                   10

<210> SEQ ID NO 3
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 3

Ile Gly Lys Glu Phe Lys Arg Ile Val Gln Arg Ile Lys Asp Phe Leu
1               5                   10                  15

Arg Asn Leu Val Pro Arg Thr Glu Ser
            20                  25

<210> SEQ ID NO 4
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 4

Phe Lys Arg Ile Val Gln Arg Ile Lys Asp Phe Leu Arg Asn Leu Val
1               5                   10                  15

<210> SEQ ID NO 5
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 5

Phe Lys Arg Ile Val Gln Arg Ile Lys Asp Phe Leu Arg
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 6

Leu Leu Gly Asp Phe Lys Arg Ile Val Gln Arg Ile Lys Asp Phe
1               5                   10                  15

<210> SEQ ID NO 7
<211> LENGTH: 16
<212> TYPE: PRT
<213> ORGANISM: Artificial Sequence
<220> FEATURE:
```

```
<223> OTHER INFORMATION: Synthetic Sequence

<400> SEQUENCE: 7

Phe Lys Arg Ile Val Gln Arg Ile Lys Asp Phe Leu Arg Asn Leu Val
1               5                   10                  15

<210> SEQ ID NO 8
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 8

Gly Leu Phe Asp Ile Ile Lys Lys Ile Ala Glu Ser Phe
1               5                   10

<210> SEQ ID NO 9
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 9

Gly Leu Phe Asp Lys Leu Lys Ser Leu Val Ser Asp Asp Lys Lys
1               5                   10                  15

<210> SEQ ID NO 10
<211> LENGTH: 21
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (14)...(21)
<223> OTHER INFORMATION: Xaa = any amino acid or no amino acid

<400> SEQUENCE: 10

Phe Lys Arg Ile Val Gln Arg Ile Lys Asp Phe Leu Arg Xaa Xaa Xaa
1               5                   10                  15

Xaa Xaa Xaa Xaa Xaa
            20

<210> SEQ ID NO 11
<211> LENGTH: 3
<212> TYPE: PRT
<213> ORGANISM: Artificial Sequence
<220> FEATURE:
<223> OTHER INFORMATION: Synthetic Sequence

<400> SEQUENCE: 11

Asn Leu Val
1

<210> SEQ ID NO 12
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 12

Arg Leu Phe Asp Lys Ile Arg Gln Val Ile Arg Lys Phe
1               5                   10
```

```
<210> SEQ ID NO 13
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 13

Gly Leu Phe Asp Ile Ile Lys Lys Ile Ala Glu Ser Phe
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (13)...(13)
<223> OTHER INFORMATION: Xaa = any amino acid

<400> SEQUENCE: 14

Gly Leu Phe Asp Ile Ile Lys Lys Ile Ala Glu Ser Xaa
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 15

Gly Leu Phe Asp Ile Ile Lys Lys Ile Ala Glu Ser Trp
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 16

Gly Leu Phe Asp Lys Leu Lys Ser Leu Val Ser Asp Asp Lys Lys
1               5                   10                  15

<210> SEQ ID NO 17
<211> LENGTH: 5
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (3)...(3)
<223> OTHER INFORMATION: Xaa = phenylglycine

<400> SEQUENCE: 17

Gly Gly Xaa Gly Gly
1               5

<210> SEQ ID NO 18
<211> LENGTH: 37
<212> TYPE: PRT
<213> ORGANISM: Artificial Sequence
<220> FEATURE:
<223> OTHER INFORMATION: Synthetic Sequence
<220> FEATURE:
```

```
<221> NAME/KEY: VARIANT
<222> LOCATION: (1)...(8)
<223> OTHER INFORMATION: Xaa = any amino acid or no amino acid
<220> FEATURE:
<221> NAME/KEY: VARIANT
<222> LOCATION: (22)...(37)
<223> OTHER INFORMATION: Xaa = any amino acid or no amino acid

<400> SEQUENCE: 18

Xaa Xaa Xaa Xaa Xaa Xaa Xaa Xaa Arg Leu Phe Asp Lys Ile Arg Gln
 1               5                  10                  15

Val Ile Arg Lys Phe Xaa Xaa Xaa Xaa Xaa Xaa Xaa Xaa Xaa Xaa Xaa
             20                  25                  30

Xaa Xaa Xaa Xaa Xaa
         35

<210> SEQ ID NO 19
<211> LENGTH: 3
<212> TYPE: PRT
<213> ORGANISM: Artificial Sequence
<220> FEATURE:
<223> OTHER INFORMATION: Synthetic Sequence

<400> SEQUENCE: 19

Val Leu Asn
 1

<210> SEQ ID NO 20
<211> LENGTH: 28
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (1)...(10)
<223> OTHER INFORMATION: Xaa = any amino acid or no amino acid
<220> FEATURE:
<221> NAME/KEY: VARIANT
<222> LOCATION: (24)...(28)
<223> OTHER INFORMATION: Xaa = any amino acid or no amino acid

<400> SEQUENCE: 20

Xaa Xaa Xaa Xaa Xaa Xaa Xaa Xaa Xaa Xaa Phe Lys Arg Ile Val Gln
 1               5                  10                  15

Arg Ile Lys Asp Phe Leu Arg Xaa Xaa Xaa Xaa Xaa
             20                  25
```

US 7,985,836 B2

ANTIMICROBIAL PEPTIDES AND METHODS OF IDENTIFYING THE SAME

This application is a divisional application of U.S. application Ser. No. 11/586,943, filed on Oct. 26, 2006, now U.S. Pat. No. 7,465,784. The foregoing application is incorporated by reference herein.

FIELD OF THE INVENTION

The present invention relates to the field of antimicrobial agents and the treatment of bacterial infections. More specifically the invention provides antimicrobial peptides and methods of identifying the same. Also provided are methods of using such peptides for the treatment of disease such as cancer.

BACKGROUND OF THE INVENTION

The search for novel antimicrobial agents is intensifying, in response to both the threat of microbial pathogens in bioterrorism and the increasing development of drug resistance to antibiotic therapeutics currently in use. Antimicrobial peptides are essential host defense molecules found in a wide variety of species and are promising antibacterial therapeutic candidates (Zasloff, M. (2002) Nature, 415:389-395; McPhee et al. (2005) J. Pept. Sci., 11:677-687). Several hundreds of antimicrobial peptides have been identified in a variety of life forms ranging from bacteria, fungi, plants, amphibians, to mammals, including humans (Mygind et al. (2005) Nature, 437:975-80; Brahmachary et al. (2004) Nucleic Acids Res., 32:D586-589; Wang et al. (2004) Nucleic Acids Res., 32:D590-D592). In mammals, cathelicidins and defensins are the two major types of host defense peptides (Zanetti, M. J. (2004) Leukoc. Biol., 75:39-48). Defensins usually contain three pairs of disulfide bonds that stabilize the protein fold. Cathelicidins, however, are rather variable in both sequence and structure, although their precursor proteins share a common N-terminal "cathelin" domain. Cathelicidins are classified into three groups. The first group of cathelicidin peptides contains 12-18 residues with beta-hairpin structures stabilized by one or two disulfide bonds. This group also includes a 13-residue linear peptide with a high content of tryptophans. The second group contains 23-37 residues and has the potential to form a helical structure. The peptides in the third group such as PR-39 are rich in prolines with 39-80 residues (for a review, see Zanetti, M. J. (2004) Leukoc. Biol., 75:39-48).

LL-37 is the only human cathelicidin identified to date. LL-37 is 37 amino acids in length and has two leucines at its N-terminus. It has been detected in a variety of cells such as B cells, monocytes, mast cells, and immature neutrophils (Sorensen et al. (1997) Blood, 90:2796-2803; Agerberth et al. (2000) Blood, 96:3086-3093; Di Nardo et al. (2003) J. Immunol., 170:2274-2278). Several lines of evidence support the significance of this human peptide in host defense. First, the precursor gene of LL-37 (hCAP-18) is up-regulated in skin in response to cutaneous infection as well as in inflammatory skin disorders such as psoriasis (Dorschner et al. (2001) Invest. Dermatol., 117:91-97; Frohm et al. (1997) J. Biol. Chem., 272:15258-15263). Second, LL-37 deficiency in neutrophils correlates with the occurrence of chronic periodontal diseases in patients with morbus Kostmann (Putsep et al. (2002) Lancet, 360:1144-1149). Third, gene knockout of the CRAMP cathelicidin in mice increases their susceptibility to skin infection (Nizet et al. (2001) Nature, 414:454-457). Fourth, expression of additional cathelicidins by gene transfer protects against skin infection by bacteria (Lee et al. (2005) Proc. Natl. Acad. Sci. U.S.A., 102:3750-3755). In addition to its antibacterial effects, human LL-37 appears to play an important role in angiogenesis, chemotaxis, and signal transduction as well (Zanetti, M. J. (2004) Leukoc. Biol., 75:39-48; Bowdish et al. (2004) J. Immunol., 172:3758-3765; Tjabring a et al. (2003) J. Immunol., 171:6690-6696). Further, after secretion onto the skin surface, human LL-37 in sweat can be cleaved (e.g., after residue F6 or R7) into more active antibacterial and antifungal fragments with a reduced toxicity to erythrocytes (Murakami et al. (2004) J Immunol., 172:3070-3077). Further, these shorter forms of LL-37 lost their capability of stimulating a host response possessed by the full-length peptide. This important observation indicates that a potent antibacterial region can be identified within LL-37 as a peptide template for therapeutic use.

According to previous circular dichroism (CD) studies, LL-37 forms helical structures upon increasing peptide concentration, anions, pH, detergents, and lipids (Johansson et al. (1998) J. Biol. Chem., 273:3718-24; Oren et al. (1999) Biochem. J., 341:501-13). The helicity of the peptide was found to correlate with antibacterial activity. Recent solid-state NMR, differential scanning calorimetry, and biochemical analysis substantiated the interactions of LL-37 with lipid bilayers (Johansson et al. (1998) J. Biol. Chem., 273:3718-24; Oren et al. (1999) Biochem. J., 341:501-13; Henzler-Wildman et al. (2004) Biochemistry, 43:8459-69; Henzler-Wildman et al. (2003) Biochemistry, 42:6545-58). Three-dimensional structure is essential for understanding the mechanism of action of the peptide. However, no three-dimensional structure has been reported for LL-37.

SUMMARY OF THE INVENTION

In accordance with the instant invention, antimicrobial peptides, compositions comprising the same, and methods of use thereof are provided. In a particular embodiment, the antimicrobial peptide has at least 90% homology with amino acid sequence FKRIVQRIKDFLRX$_1$ (SEQ ID NO: 10), wherein X$_1$ is selected from the group consisting of 0, 1, 2, 3, 4, 5, 6, 7, and 8 amino acids. The amino acid sequence of the peptides may also be in reverse orientation. In another embodiment, the antimicrobial peptide has at least 90% homology with amino acid sequence X$_1$RLFDKIRQVIRKFX$_2$ (SEQ ID NO: 18), wherein X$_1$ is 0, 1, 2, 3, 4, 5, 6, 7, or 8 amino acids and X$_2$ is 0, 1, 2, 3, 4, 5, 6, 7, 8, 9, 10, 11, 12, 13, 14, 15, or 16 amino acids. The peptides of the instant invention may comprise at least one D-amino acid.

Nucleic acid molecules encoding the antimicrobial peptides of the instant invention are also provided. In a particular embodiment, the antimicrobial peptides and nucleic acid molecules encoding the same are contained within a pharmaceutical composition with a pharmaceutically acceptable carrier. In still another embodiment, methods for treating a bacterial infection or cancer in a patient comprising administering the pharmaceutical compositions of the instant invention are provided.

In accordance with another aspect of the instant invention, methods for identifying a core active peptide region of a peptide of interest are provided. The methods comprise performing a spectroscopy analysis of the peptide of interest; identifying disordered residues, if any, from the spectroscopy analysis; and removing the identified residues, if any, from the peptide of interest, thereby identifying the core active peptide region.

BRIEF DESCRIPTIONS OF THE DRAWING

FIGS. 1A and 1B are the TOCSY (total correlation spectroscopy) spectra of LL-37(13-37) (FIG. 1A) and LL-37(17-32) (FIG. 1B) in SDS micelles. FIG. 1C is a general schematic of the TOCSY-trim process.

Figure 2:
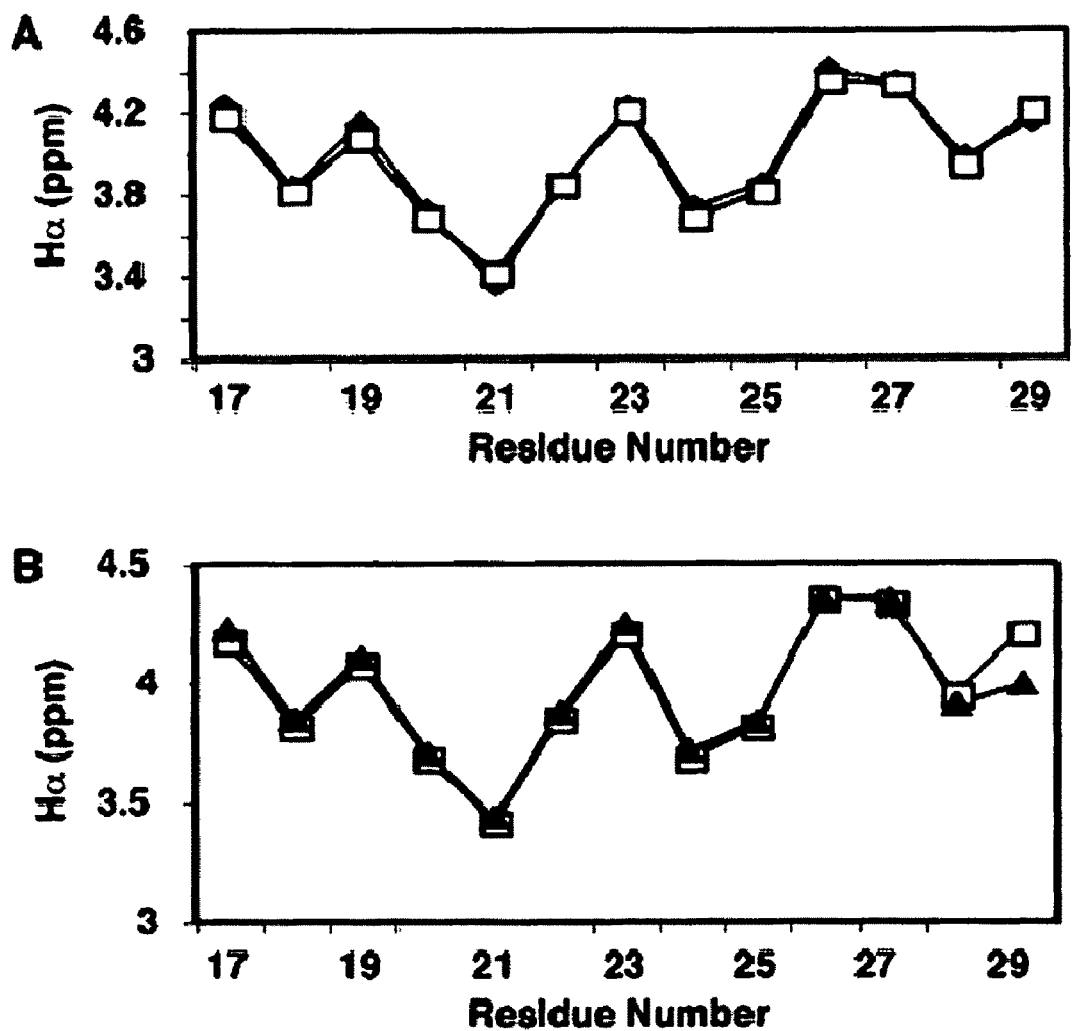

FIGS. 2A and 2B are graphical representations of the effects of membrane-mimetic environments (FIG. 2A) and peptide length (FIG. 2B) on the structure of the LL-37 core region. Hα chemical shifts for residues 17-29 measured using LL-37(17-29) in SDS micelles (□ in both FIGS. 2A and 2B), in dioctanoyl phosphatidylglycerol micelles (♦ in FIG. 2A), and measured using LL-37(13-37) in SDS micelles (▲ in FIG. 2B).

FIGS. 3A-3C are structures of the LL-37 core peptide (FIG. 3A) and comparison with aurein 1.2 (FIG. 3B; Rozek et al. (2000) Eur. J. Biochem., 267:5330-5341) and a bacterial membrane anchor from the N-terminus of glucose-specific enzyme IIA of *E. coli* (FIG. 3C; Wang, et al. (2000) J. Biol. Chem., 275:39811-39814). To facilitate the comparison, the order of the N- and C-end of the LL-37 core peptide is reversed. The Protein Data Bank accession codes for the coordinates of aurein 1.2 and the membrane anchor are 1VM5 (Wang et al. (2005) J. Biol. Chem., 280:5803-5811) and 1053 (Wang et al. (2003) Protein Sci., 12:1087-1096).

Figure 4:
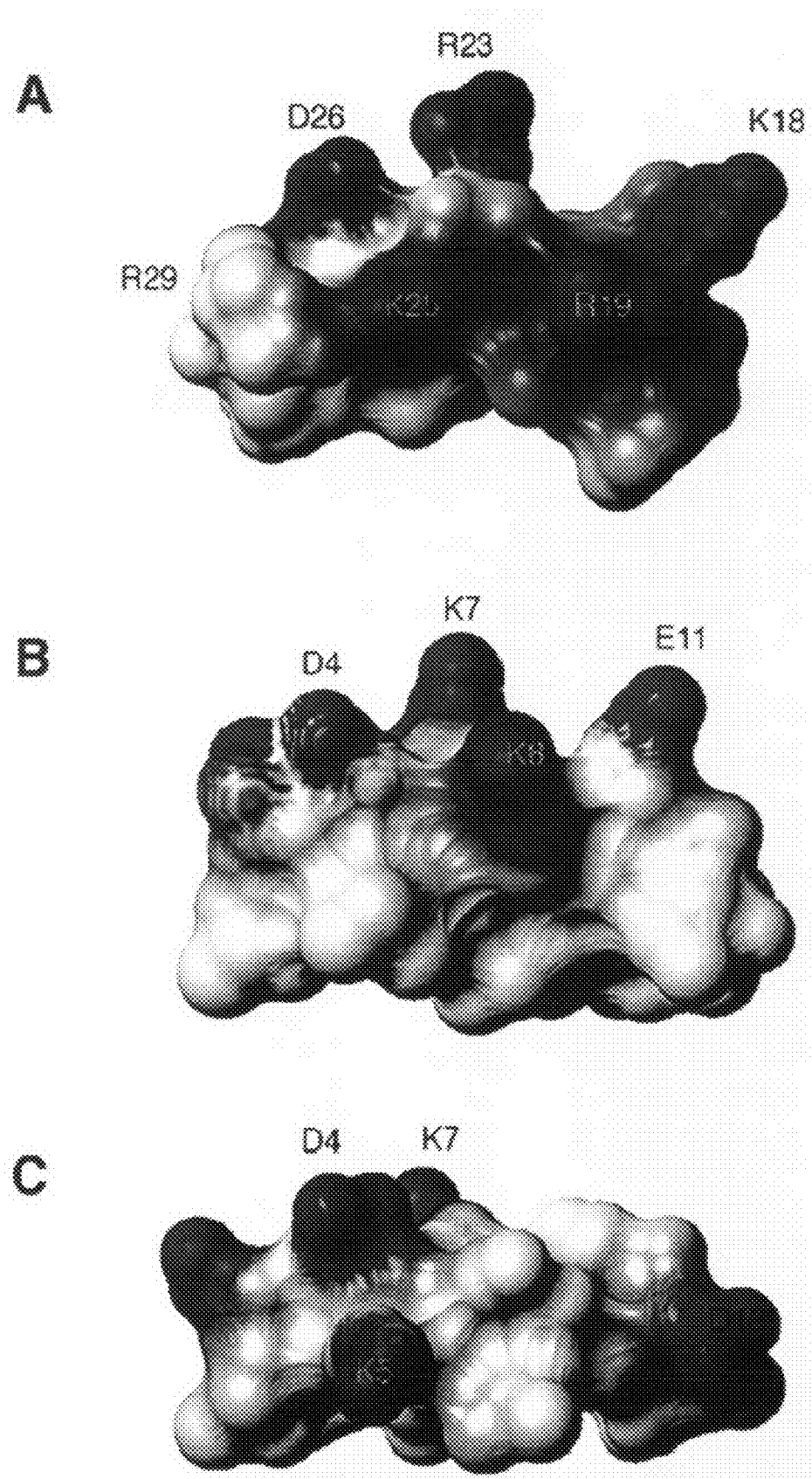

FIGS. 4A-4C are schematic drawings of the potential surfaces of the LL-37 core peptide (FIG. 4A), aurein 1.2 from a frog (FIG. 4B), and the bacterial membrane anchor from *E. coli* (FIG. 4C). The figures were made using MOLMOL (Koradi et al. (1996) J. Mol. Graphics, 14:51-55).

FIGS. 5A and 5B are graphical representations of portions of the NOESY spectra (mixing time 100 ms) of LL-37(1-12) at 15° C. (FIG. 5A) and LL-37(13-37) in SDS micelles at 25° C. (FIG. 5B), both at pH 5.4. NMR signals were assigned based on the established method (Wuthrich, K. NMR of Proteins and Nucleic Acids; Wiley: New York, 1986). Intraresidue cross-peaks are labeled with the single-letter amino acid code. Interresidue NOE cross-peaks between Hα and amide protons are labeled with arabic numbers. For example, 21/25 stands for the NOE cross-peak from the Hα proton of V21 to the backbone amide proton of K25.

Figure 6:
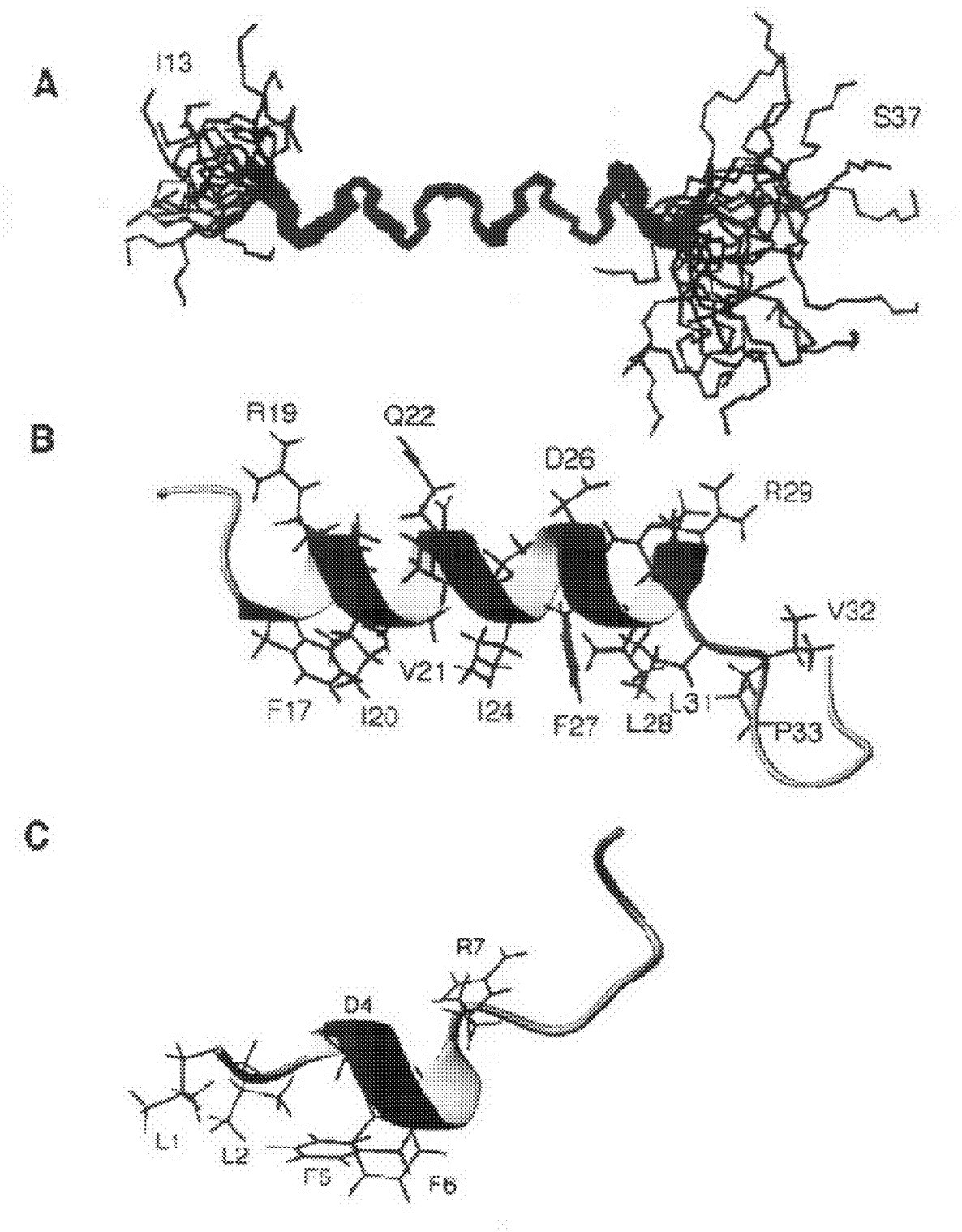

FIGS. 6A-6C are schematic drawings of the solution structures of the N- and C-terminal fragments of LL-37 bound to SDS micelles. Structures were determined as described hereinbelow. Shown are the backbone (with residues 17-29 superimposed; FIG. 6A) and ribbon (FIG. 6B) representations of the structure of LL-37(13-37) and a ribbon view of the structure of LL-37(1-12) (FIG. 6C). The aromatic-aromatic interactions between F5 and F6 in LL-37(1-12) are proposed to be essential for LL-37 aggregation (Johansson et al. (1998) J. Biol. Chem., 273:3718-24; Oren et al. (1999) Biochem. J., 341:501-13).

FIGS. 7A-7C are graphical representations of portions of the NOESY spectra of the N-terminal fragment LL-37(1-12) (FIG. 7A), the C-terminal fragment LL-37(13-37) (FIG. 7B), and full-length LL-37 (FIG. 7C) in SDS micelles for peptide-aided signal assignments (PASA). Vertical lines indicate the Hδ protons of aromatic residues F5, F6, F17, and F27. Some NOE cross-peaks from the Hδ protons of the aromatic rings to nearby hydrophobic side chains are also labeled. The similar chemical shifts between the fragments and intact LL-37 enabled partial assignments.

Figure 8:
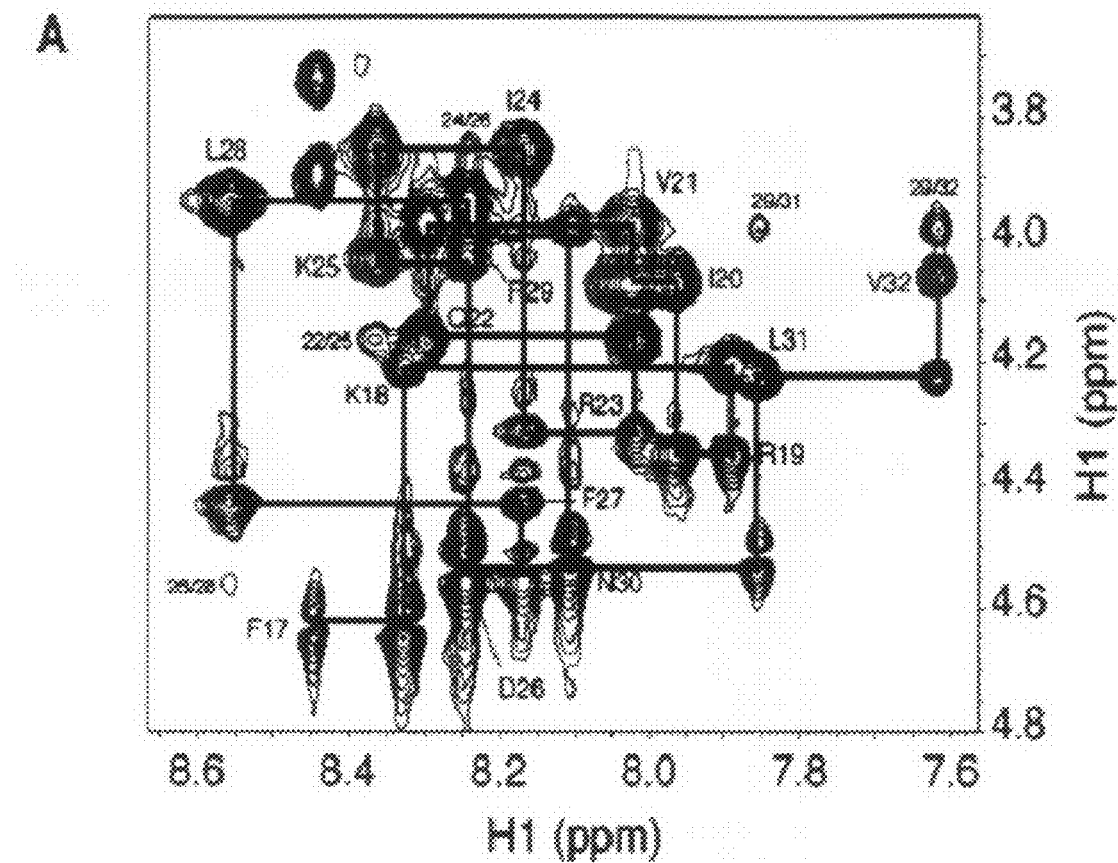
Figure 8:
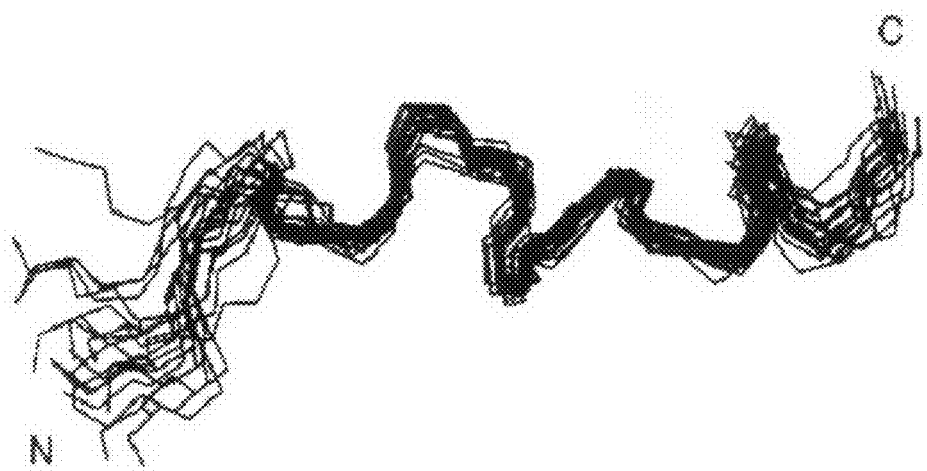

FIG. 8A is a graphical representation of a portion of the NOESY spectrum of LL-37(17-32) with D-amino acids at I20, I24, and L28. The NOE pattern for the D-peptide (FIG. 8A) is clearly different from that of the corresponding region of the L-diastereomer in FIG. 5B. The phases of the cross-peaks of F17, D26, F27, and N30 in the vicinity of water were influenced by a water flipback pulse. FIG. 8B provides a schematic drawing of the 3D structure of LL-37(17-32) consisting of a twisted omega turn at the N-terminus and a $3_{10}$ helix at the C-terminus. This structure is also different from that shown in FIG. 6B, which is entirely helical for the same portion of the peptide.

Figure 9:
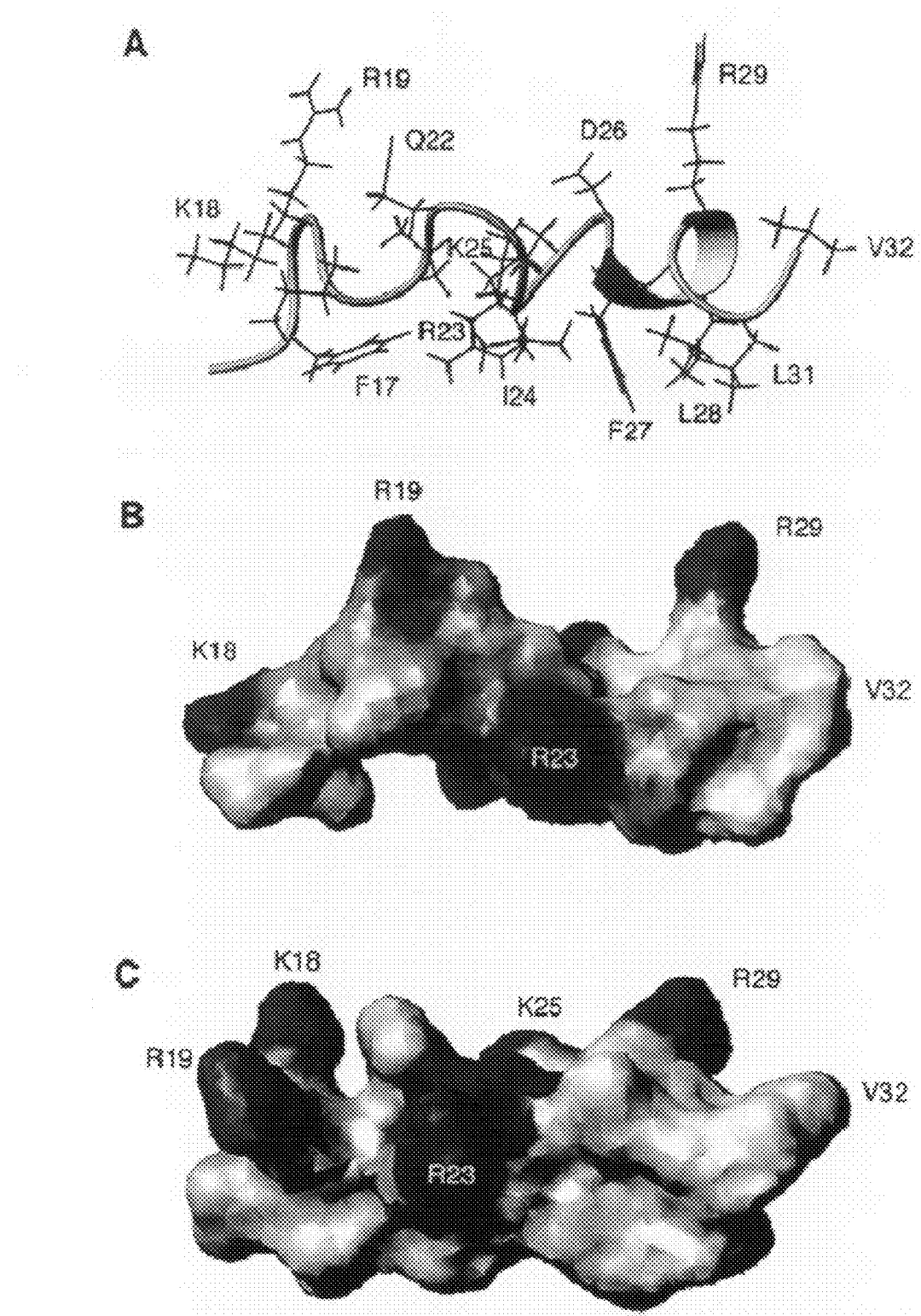

FIGS. 9A-9C provide schematic drawings of the structural basis of detoxification of LL-37(17-32) by introducing D-amino acids. Although the D-peptide retains an amphipathic structure (FIG. 9A) and identical toxic effects on bacteria (Table 2), the hydrophobic defect in the D-peptide elucidated by structural determination (FIG. 9B) caused the loss of toxic effects on human cells. Similar hydrophobic defects do not occur in the structure of the corresponding L-diastereomer (FIG. 9C).

Figure 10:
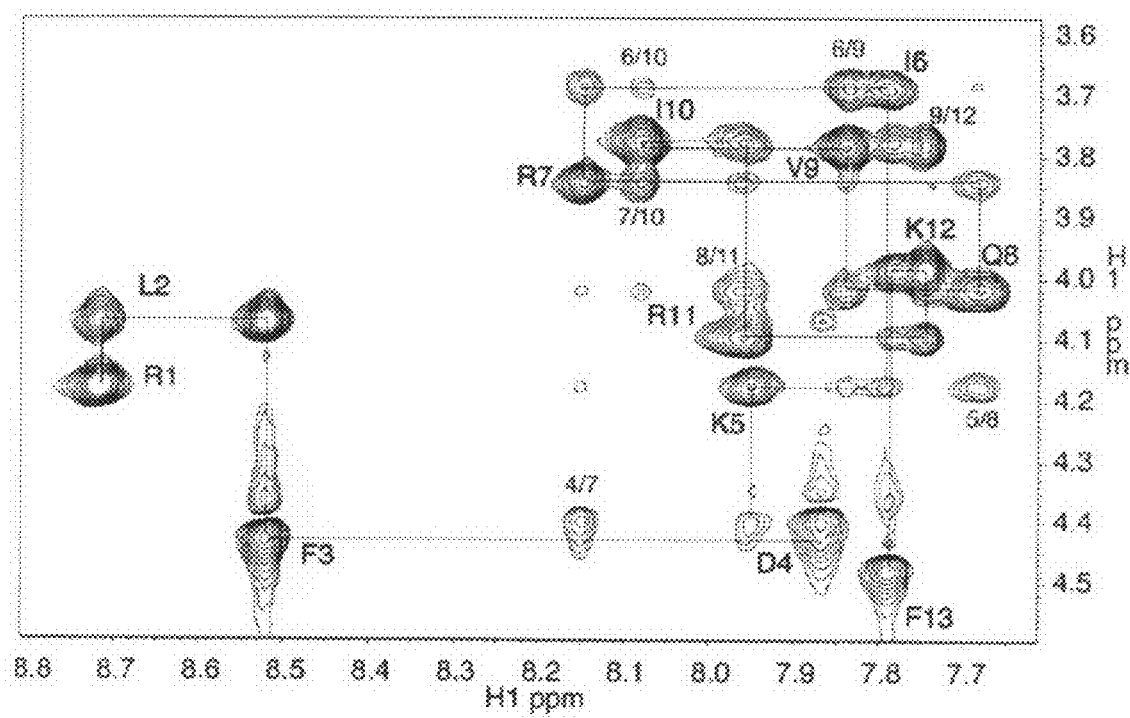

FIG. 10 is a graphical representation of the fingerprint region of the NOESY spectrum (mixing time 100 ms) of LL-37-derived aurein 1.2 analog (i.e., retro-peptide of LL-37 (17-29)) in sodium dodecyl sulfate (SDS) at a peptide/SDS ratio of 1:40, pH 4.4, and 25° C. The HN-Hα NOE cross peak for each residue is labeled using the single-lettered amino-acid code. The constructs show sequential signal assignments. Also labeled are key inter-residue NOE cross peaks of (i, i+3) and (i, i+4) types, indicative of a helical structure. The cross-peak label scheme is identical to that in FIG. 5). A similar NOE connectivity pattern was observed at pH 5.4 as well.

FIGS. 11A-11C are graphical representations of the $H^\alpha$ (FIG. 11A), $C^\alpha$ (FIG. 11B), and $C^\beta$ (FIG. 11C) secondary shift plots for the micelle bound LL-37-derived aurein 1.2 analog (LLAA). Secondary shifts are the chemical shift differences between the measured and random-coil shifts. Heteronuclear chemical shifts for LLAA were obtained from natural abundance 2D correlated spectra. All these plots suggest a helical structure for residues 2-12 of peptide LLAA.

FIGS. 12A-12C provide schematic drawings of the structure of the LL-37-derived aurein 1.2 analog (LLAA) bound to SDS micelles at pH 4.4 and 25° C. determined by solution NMR spectroscopy and refined by chemical shift derived backbone angles. Shown are the backbone (FIG. 12A), backbone and side chains (FIG. 12B) of LLAA with residues 2-12 superimposed, and a ribbon diagram (FIG. 12C) for a representative structure with side chains selectively labeled.

FIG. 13A is the chemical structure of dioctanoyl phosphatidylglycerol (D8PG). FIG. 13B is a graphical representation of the intermolecular NOE cross peaks between F3 of the bacterial membrane anchor and didecanoyl phosphatidylglycerol (D10PG) at pH 5.4. Similar effects were observed between the membrane anchor and dihexanoyl phosphatidylglycerol (DHPG) (Wang et al. (2003) Protein Sci., 12:1087-1096). FIG. 13C is a graphical representation of the intermolecular NOE cross peaks between F3 and F13 of the LL-37-derived aurein 1.2 analog (LLAA) and D8PG at pH 7. Intermolecular NOESY spectra were recorded at a peptide/lipid molar ratio of 1:5 and 25° C. For clarity, only intermolecular NOE cross peaks were selectively labeled with peptide resonances at the top of the panels and lipid signals by the peaks.

DETAILED DESCRIPTION OF THE INVENTION

To provide structural insight into the multiple functions of this important human defense peptide, the structures of certain fragments of LL-37 were solved in complex with detergent micelles, which mimic bacterial membranes (Henry et al. (1994) Methods Enzymol., 239:515-535; Opella et al.

(2004) Chem. Rev. 104:3587-3606). The use of sodium dodecylsulfate (SDS) is supported by the identical Hα chemical shifts of the peptides in SDS and phosphatidylglycerols (Wang et al. (2003) Protein Sci., 12:1087-1096; Wang et al. (2005) J. Biol. Chem., 280:5803-5811; Li et al. (2006) J. Am. Chem. Soc., 128:5776-5785). The quality of micelle-bound structures was improved by utilizing natural abundance chemical shifts (Wang et al. (2005) J. Biol. Chem., 280:5803-5811). Furthermore, a short antibacterial fragment within LL-37 is described herein which was determined by TOCSY-trim, a technique described hereinbelow that effectively trims nonessential membrane-targeting peptide regions based on the TOCSY patterns of side-chain resonances. The instant invention also demonstrates that it is feasible to detoxify LL-37 fragments by introducing D-amino acids. Indeed, without being bound by theory, it can be proposed that D-amino acid generate hydrophobic defects within the peptide, because of the incoherent packing of hydrophobic clusters, and thereby disrupt the binding of the D-peptide to human cells.

Herein, LL-37 was dissected into fragments (Table 1) by TOCSY-trim to understand the structure-activity relationship. A short helix was found in the N-terminal fragment, LL-37(1-12). This single hydrophobic cluster in the N-terminal peptide is not toxic to either bacteria or cancer cells (Table 2). In contrast, the C-terminal fragment, LL-37(13-37), kills both bacteria and cancer cells. The solution structure of LL-37(13-37) contains a well-defined central helix with both ends "frayed" (FIG. 6A). This central amphipathic helix (FIG. 6B) is responsible for the antibacterial and anticancer activity of LL-37, because the disordered regions at both ends can be deleted with little influence on the antibacterial activity of the peptide. This structured central region of LL-37 (also supported by TALOS (torsion angle likelihood obtained from shift and sequence similarity program) analysis) corresponds well to the shortest LL-37 core antibacterial peptide identified by TOCSY-trim (FIGS. 1A-1C). Thus, TOCSY-trim proves to be a useful technique for efficient identification of a core membrane-targeting antimicrobial peptide hidden in a longer polypeptide sequence prior to the completion of structural determination. Because only a few peptides (Table 1) were synthesized, TOCSY-trim is cost-effective in trimming of nonessential membrane-targeting regions from long peptides.

The structural similarities (FIGS. 3 and 4) of the LL-37 core peptide to other peptides such as the bacterial membrane anchor discovered in *Escherichia coli* glucose-specific enzyme IIA and aurein 1.2 isolated from the Australian Bell Frog *Lithoria aurea* (Rozek et al. (2000) Eur. J. Biochem., 267:5330-5341), allow for a better understanding of the antibacterial activity of LL-37. Due to the equivalent hydrophobic surfaces, higher antibacterial activity of the LL-37 core peptide (FIG. 3A) than that of aurein 1.2 (FIG. 3B) is attributed to additional cationic side chains in the former (5 vs 2), which prefer negatively charged bacterial membranes. In contrast, the higher activity of aurein 1.2 than that of the bacterial membrane anchor (inactive) was determined by a higher hydrophobicity of the former than that of the latter (Table 1), since both peptides have two cationic lysines in the membrane-binding helical domains.

Incorporation of D-amino acids could diminish the cytotoxicity of the LL-37 peptides without sacrificing its toxic effect on bacteria. Therefore, it is feasible to design selective antibacterial peptides using human LL-37 as a template. The structural basis for this detoxification has been elucidated. D-Amino acids disrupted the canonical helical structure (Mitchell et al. (2003) Proteins, 50:563-571) by distorting the peptide backbone (FIG. 9A). The out-of-phase packing of the two aromatic-residue-involved hydrophobic clusters caused hydrophobic defects in the amphipathic structure of dLL-37 (17-32), leading to a poor hydrophobicity (Table 1) and rendering it insufficient for targeting human cells (Table 2). It is noteworthy that the poor hydrophobicity of the bacterial membrane anchor is due to a short amphipathic helix (FIG. 3C) as well as a narrow hydrophobic surface (FIG. 4C). In conclusion, reduction in peptide hydrophobicity could be a fundamental approach for improving cell selectivity of antimicrobial peptides, whether it is achieved by decreasing the content of hydrophobic residues (FIG. 3C) or by D-amino acid incorporation (FIG. 9A). This unified concept for improving peptide selectivity by tuning hydrophobicity is useful for designing potent antimicrobial peptides, thereby providing an efficacious alternative to traditional antibiotics. Such peptides are particularly useful as a replacement for treatment of antibiotic-resistant infections.

I. Definitions

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

A "replicon" is any genetic element, for example, a plasmid, cosmid, bacmid, plastid, phage or virus, that is capable of replication largely under its own control. A replicon may be either RNA or DNA and may be single or double stranded. Generally, a "viral replicon" is a replicon which contains the complete genome of the virus. A "sub-genomic replicon" refers to a viral replicon that contains something less than the full viral genome, but is still capable of replicating itself. For example, a sub-genomic replicon may contain most of the genes encoding for the non-structural proteins of the virus, but not most of the genes encoding for the structural proteins.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g., chromatographic methods, agarose or polyacrylamide gel electrophoresis, HPLC analysis, and the like).

The term "oligonucleotide" as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as appropriate temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

Polymerase chain reaction (PCR) has been described in U.S. Pat. Nos. 4,683,195, 4,800,195, and 4,965,188, the entire disclosures of which are incorporated by reference herein.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., 1989, Molecular Cloning: A Laboratory Manual, Cold Spring Harbor Laboratory Press):

$$T_m = 81.5°\text{ C.} + 16.6 \text{ Log }[\text{Na+}] + 0.41(\% \text{ G+C}) - 0.63 (\% \text{ formamide}) - 600/\#\text{bp in duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5× Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5× Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5× Denhardt's solution, 0.5% SDS and 100 µg/ml denatured salmon sperm DNA at 42° C., and washed in 0.1× SSC and 0.5% SDS at 65° C. for 15 minutes.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, or the addition of stabilizers.

The term "gene" refers to a nucleic acid comprising an open reading frame encoding a polypeptide, including both exon and (optionally) intron sequences. The nucleic acid may also optionally include non-coding sequences such as promoter or enhancer sequences. The term "intron" refers to a DNA sequence present in a given gene that is not translated into protein and is generally found between exons.

II. Peptides

LL-37 peptides of the present invention may be prepared in a variety of ways, according to known methods. The proteins may be purified from appropriate sources, e.g., transformed bacterial or animal cultured cells or tissues, by immunoaffinity purification. The availability of nucleic acid molecules encoding the LL-37 peptide enables production of the protein using in vitro expression methods and cell-free expression systems known in the art. In vitro transcription and translation systems are commercially available, e.g., from Promega Biotech (Madison, Wis.) or Gibco-BRL (Gaithersburg, Md.).

Larger quantities of LL-37 peptides may be produced by expression in a suitable prokaryotic or eukaryotic system. For example, part or all of a DNA molecule encoding for LL-37 may be inserted into a plasmid vector adapted for expression in a bacterial cell, such as E. coli. Such vectors comprise the regulatory elements necessary for expression of the DNA in the host cell positioned in such a manner as to permit expression of the DNA in the host cell. Such regulatory elements required for expression include promoter sequences, transcription initiation sequences and, optionally, enhancer sequences.

LL-37 peptides produced by gene expression in a recombinant prokaryotic or eukaryotic system may be purified according to methods known in the art. A commercially available expression/secretion system can be used, whereby the recombinant protein is expressed and thereafter secreted from the host cell, and readily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope or the hemagglutinin epitope. Such methods are commonly used by skilled practitioners.

Li et al. (Protein Exp. Purif. (2006) 47:498-505) provides exemplary methods for the production and purification of LL-37 peptides.

LL-37 peptides of the invention, prepared by the aforementioned methods, may be analyzed according to standard procedures. For example, such protein may be subjected to amino acid sequence analysis, according to known methods.

An exemplary amino acid sequence of human LL-37 is

LLGDFFRKSKEKIGKEFKRIVQRIKDFLRNLVPRTES. (SEQ ID NO: 1)

The amino acid sequence of the LL-37 peptides (fragments) of the instant invention may have at least 75%, 80%, 85%, 90%, 95%, 97%, 99%, or 100% homology with SEQ ID NO: 1, particularly at least 90% homology. In a particular embodiment, the LL-37 peptide has at least 75%, 80%, 85%, 90%, 95%, 97%, 99%, or 100% homology with:

FKRIVQRIKDFLRX$_1$, (SEQ ID NO: 10)

wherein X$_1$ is 0, 1, 2, 3, 4, 5, 6, 7, or 8 amino acids, particularly 0, 1, 2, 3, 4, or 5 amino acids. In a particular embodiment, X$_1$ is the sequence NLV (SEQ ID NO: 11). The amino acids of X$_1$ may be selected to correspond with the full-length LL-37 (e.g., if X$_1$ is one amino acid, it would preferably be N, asparagine). The LL-37 peptide of SEQ ID NO: 10 may also be in reverse orientation (e.g., RLFDKIRQVIRKF. (SEQ ID NO: 12))

LL-37 peptides of the instant invention may also have at least 75%, 80%, 85%, 90%, 95%, 97%, 99%, or 100% homology with:

X$_1$RLFDKIRQVIRKFX$_2$, (SEQ ID NO: 18)

wherein X$_1$ is 0, 1, 2, 3, 4, 5, 6, 7, or 8 amino acids and X$_2$ is 0, 1, 2, 3, 4, 5, 6, 7, 8, 9, 10, 11, 12, 13, 14, 15, or 16 amino acids, particularly 0, 1, 2, 3, 4, or 5 amino acids. In a particular embodiment, X$_1$ is 0 amino acids or the sequence VLN (SEQ ID NO: 19) and X$_2$ is 0 amino acids. The amino acids of X$_1$ and X$_2$ may be selected to correspond with the full-length LL-37 in reverse orientation (e.g., if X$_1$ is one amino acid, it would preferably be N, asparagine).

In a another embodiment, the LL-37 peptide has at least 75%, 80%, 85%, 90%, 95%, 97%, 99%, or 100% homology with:

X$_1$FKRIVQRIKDFLRX$_2$, (SEQ ID NO: 20)

wherein X$_1$ and X$_2$ are each 0, 1, 2, 3, 4, 5, 6, 7, 8, 9, or 10 amino acids, particularly 0, 1, 2, 3, 4, or 5 amino acids, particularly 0, 1, or 2 amino acids. The amino acids of X$_1$ and X$_2$ may be selected to correspond with the full-length LL-37.

The LL-37 peptides of the instant invention may contain substitutions to the amino acids of SEQ ID NO: 1. These substitutions may be similar to the amino acid present in SEQ ID NO: 1 (e.g., an acidic amino acid in place of another acidic amino acid, a basic amino acid in place of a basic amino acid, a large hydrophobic amino acid in place of a large hydrophobic, etc.). The substitutions may comprise amino acid analogs and mimetics. Exemplary substitutions to LL-37 are provided in WO/2004/067563 and Nell et al. (Peptides (2006) 27:649-60). In a particular embodiment, the substitutions are predicted to promote helicity or helix formation. In a preferred embodiment, the peptides retain their antimicrobial activity.

The LL-37 peptides of the instant invention may have capping, protecting and/or stabilizing moieties at the C-terminus and/or N-terminus. Such moieties are well known in the art and include, without limitation, amidation and acetylation. The peptide template may also be lipidated or glycosylated at any amino acid (i.e., a glycopeptide).

The LL-37 peptides of the instant invention may also comprise at least one D-amino acid instead of the native L-amino acid. The LL-37 peptides may comprise only D-amino acids. In a particular embodiment, the LL-37 peptides comprise D-amino acids which are spaced apart by about 3 consecutive L-amino acids. In yet another embodiment, at least one of I20, I24, and L28, preferably all 3, is a D-amino acid.

III. Nucleic Acid Molecules

Nucleic acid molecules encoding the LL-37 peptides of the invention may be prepared by any method known in the art such as (1) synthesis from appropriate nucleotide triphosphates or (2) isolation and/or amplification from biological sources. The availability of nucleotide sequence information enables preparation of an isolated nucleic acid molecule of the invention by oligonucleotide synthesis. Indeed, knowledge of the amino sequence is sufficient to determine an encoding nucleic acid molecule. Synthetic oligonucleotides may be prepared by the phosphoramidite method employed in the Applied Biosystems 38A DNA Synthesizer or similar devices. The resultant construct may be purified according to methods known in the art, such as gel electrophoresis or high performance liquid chromatography (HPLC).

Nucleic acid sequences encoding the LL-37 peptides of the invention may be isolated from appropriate biological sources using methods known in the art. In one embodiment, a cDNA clone of LL-37 is isolated from a cDNA expression library, preferably of human origin, and modified to create the LL-37 peptides of the instant invention. In an alternative embodiment, utilizing the sequence information provided by the cDNA sequence, genomic clones encoding LL-37 may be isolated.

Nucleic acids of the present invention may be maintained in any convenient vector, particularly an expression vector. Different promoters may be utilized to drive expression of the nucleic acid sequences based on the cell in which it is to be expressed. Antibiotic resistance markers are also included in these vectors to enable selection of transformed cells. LL-37 peptide encoding nucleic acid molecules of the invention include cDNA, genomic DNA, RNA, and fragments thereof which may be single- or double-stranded. Thus, this invention provides oligonucleotides having sequences capable of hybridizing with at least one sequence of a nucleic acid molecule of the present invention.

Also encompassed in the scope of the present invention are oligonucleotide probes which specifically hybridize with the LL-37 peptide nucleic acid molecules of the invention. Primers capable of specifically amplifying LL-37 peptide encoding nucleic acids described herein are also contemplated herein. Such oligonucleotides are useful as probes and primers for detecting, isolating or amplifying LL-37 peptide encoding nucleic acids.

It will be appreciated by persons skilled in the art that variants (e.g., allelic variants) of LL-37 sequences exist, for example, in the human population, and must be taken into account when designing and/or utilizing oligonucleotides of the invention. Accordingly, it is within the scope of the present invention to encompass such variants, with respect to the LL-37 peptide sequences disclosed herein or the oligonucleotides targeted to specific locations on the respective genes or RNA transcripts. Accordingly, the term "natural allelic variants" is used herein to refer to various specific nucleotide sequences of the invention and variants thereof that would occur in a human population. The usage of different wobble codons and genetic polymorphisms which give rise to conservative or neutral amino acid substitutions in the encoded protein are examples of such variants. Such variants would not demonstrate substantially altered LL-37 activity or protein levels.

IV. Uses of the LL-37 Peptides

The present invention also encompasses pharmaceutical compositions comprising at least one LL-37 peptide in a pharmaceutically acceptable carrier. Such a pharmaceutical composition may be administered, in a therapeutically effective amount, to a patient in need thereof. The pharmaceutical compositions of the present invention can be administered by any suitable route, for example, by injection, by oral, pulmonary, nasal, topical, or other modes of administration such as controlled release devices. In general, pharmaceutical compositions and carriers of the present invention comprise, among other things, pharmaceutically acceptable diluents, preservatives, stabilizing agents, solubilizers, emulsifiers, adjuvants and/or carriers. Such compositions can include diluents of various buffer content (e.g., saline, Tris HCl, acetate, phosphate), pH and ionic strength; and additives such as detergents and solubilizing agents (e.g., Tween 80, Polysorbate 80), anti oxidants (e.g., ascorbic acid, sodium metabisulfite), preservatives (e.g., Thimersol, benzyl alcohol) and bulking substances (e.g., lactose, mannitol). The compositions can be incorporated into particulate preparations of polymeric compounds such as polylactic acid, polyglycolic acid, etc., or into liposomes. Such compositions may influence the physical state, stability, rate of in vivo release, and rate of in vivo clearance of components of a pharmaceutical composition of the present invention. Exemplary pharmaceutical compositions and carriers are provided, e.g., in "Remington's Pharmaceutical Sciences" by E. W. Martin (Mack Pub. Co., Easton, Pa.) and "Remington: The Science And Practice Of Pharmacy" by Alfonso R. Gennaro (Lippincott Williams & Wilkins, 2005) which are herein incorporated by reference. The pharmaceutical composition of the present invention can be prepared, for example, in liquid form, or can be in dried powder form (e.g., lyophilized). In a particular embodiment, the LL-37 peptides are comprised within a pharmaceutical composition suitable for topical or oral administration (e.g., gums, pastes, mouth rinses).

The present invention also encompasses methods for preventing and/or treating microbial infections. The pharmaceutical compositions of the instant invention can be administered to an animal, in particular a mammal, more particularly a human, in order to treat a microbial infection. In particular, the pharmaceutical compositions are used to prevent and/or treat bacterial infections, particularly dental infections. The pharmaceutical compositions of the instant invention may also comprise at least one other anti-microbial agent (e.g., anti-bacterial agents such as antibiotics).

The present invention also encompasses methods for tumor suppression. Specifically, a therapeutically effective amount of at least one LL-37 peptide can be administered to a patient, in need thereof, for the treatment of cancer. Cancers that may be treated using the present protocol include, but are not limited to: prostate cancers, colorectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma. In a particular embodiment, the pharmaceutical composition may further comprise at least one chemotherapeutic agent. In yet another embodiment, the pharmaceutical compositions for the treatment of cancer may be formulated by direct injection into the tumor.

V. TOCSY-trim

TOCSY-trim is a technique that effectively trims nonessential membrane-targeting peptide regions based on the patterns of side-chain resonances. More particularly, TOCSY-trim is a technique that identifies disordered or weakly micelle-binding peptide regions based on strong cross-peaks (e.g., see residues 34-37 in FIGS. 1A and 30-32 in FIG. 1B).

As shown in Example 1, the trimming of such regions had small effects on the activities (e.g., antibacterial and anticancer activities) of the peptide. Accordingly, TOCSY-trim is clearly useful in identifying a core, active peptide embedded in a longer sequence. One particular advantage of TOCSY-trim is that a core peptide region (e.g., membrane-binding peptide region) could be mapped quickly and efficiently without the completion of 3D structure determination, which is usually a long and difficult task.

As described hereinbelow as an example of the TOCSY-trim process, LL-37 and its fragments were chemically synthesized and proton-based TOCSY spectra were analyzed. Residues exhibiting strong cross-peaks were removed from the peptides, thereby identifying a minimal membrane-targeting region.

Although the use of TOCSY is exemplified herein, the instant invention encompasses other types of spectroscopy which reveal information about the structure and dynamics of a protein or peptide. Exemplary spectroscopy methods include, without limitation, TOCSY, two-dimensional nuclear magnetic resonance (NMR), nuclear Overhauser enhancement spectroscopy (NOESY), double-quantum filtered correlation spectroscopy (DQF-COSY), correlation spectroscopy (COSY), transverse relaxation optimized spectroscopy (TROSY), heteronuclear single quantum coherence (HSQC), heternuclear NOE, HNCO, CBCA(CO)NH, combinations of the above, and the like.

In a preferred embodiment, the spectroscopy of the peptide is performed in a membrane-mimetic model. Exemplary membrane-mimetic models include lipid and/or detergent micelles, lipid and/or detergent bicelles, and lipid and/or detergent bilayers. The membrane-mimetics may comprise at least one lipid and/or detergent. Exemplary detergents and lipids include, without limitation, dihexanoyl phosphatidylglycerol (DHPG), dioctanoyl phosphatidylglycerol (D8PG), didecanoyl phosphatidylglycerol (D10PG), or other phosphatidylglycerols (PG), sodium dodecylsulfate (SDS), sodium hexanesulfonate (SHS), sodium nonanesulfonate (SNS), dihexanoyl phosphatidylcholine (DHPC), or other phosphatidylcholines, dodecylphosphocholine (DPC), and lysophopholipids of any head group.

The following examples describe illustrative methods of practicing the instant invention and are not intended to limit the scope of the invention in any way.

EXAMPLE 1

Materials and Methods

Antibacterial Assays. The antibacterial activity of the LL-37 peptides and its analogues was analyzed using the standard approach of microdilution (Wang et al. (2005) J. Biol. Chem., 280:5803-5811; Yu et al. (2002) J. Pept. Res., 60:1-9). In brief, a small culture of wild type *E. coli* K12 was grown overnight. A fresh culture was inoculated with a small aliquot of the overnight culture and incubated at 37° C. until the optical density reached the mid-logarithmic stage. The culture (90 µL each) was then diluted to an $A_{600}$ of 0.001 and partitioned into a 96-well plate with ~$10^6$ cells per well. The cells were then treated with 10 µL of the peptide at a series of levels (5 to 320 µM), allowing the minimum inhibitory concentration (MIC) measurement for each. Each peptide assay was repeated 3 times. The plate was then further incubated at 37° C. overnight (~16 hours) and read on an Ultra Microplate Reader at 620 nm (Bio-TEK Instruments; Winooski, Vt.).

Anticancer Assays. Cytotoxicity studies were performed using the calorimetric MTT assays for assessing cell viability (Mark et al. (1999) Life Sci., 64:1941-1953; Hansen et al. (1989) J. Immunol. Methods, 119:203-210). Three cell lines were used, including drug-resistant KBv, drug-sensitive KB, and the nontransformed human brain microvessel endothelial cells (HBMEC). In brief, the cells were seeded onto 96-well plates at a density of 5000 cells per well. The cells were exposed to various concentrations (5-320 µM) of LL-37 peptides (triplicate assays for each) 24 hours after seeding. After 68 hours of exposure, the peptide solution was replaced with fresh media and followed by cytotoxicity analysis using the MTT assay.

The MTT assay was performed by incubating the cells with 5 mg/mL of 3-[4,5-dimethylthiazol-2-yl]-2,5-dephenyltetrazolium bromide (MTT) for 2 hours at 37° C. The cells were then solubilized in a 50:50 mixture of dimethyl formamide (DMF) and $H_2O$ containing 20% SDS (pH 4.7). The plates were read after overnight incubation. Viability is directly proportional to the amount of metabolic conversion of MTT to formazin in the mitochondria of living cells and is assessed by measuring the absorbance at 550 nm using a Microkinetics Reader (Fisher Biotech). Viability is expressed as a percent of control cells receiving only culture media without any peptides. The data from the cytotoxicity studies were plotted using Microsoft Excel, and the $LC_{50}$ (concentration resulting in 50% reduction in cell viability) and standard deviations were determined for each peptide.

Analytical Reversed-Phase HPLC. The retention time of the peptide was measured on an ISCO (Lincoln, Nebr.) HPLC system equipped with a Vydac (Hesperia, Calif.) C18 reversed-phase column (250×4.6 mm) at an ambient temperature of ~25° C. The peptide was eluted with a linear gradient of acetonitrile (containing 0.1% TFA) from 5% to 95% at a flow rate of 1 mL/min. Peptides were detected by UV absorbance at 215 nm.

NMR Spectroscopy. All peptides were synthesized and purified (>95% purity) by Genemed Synthesis, Inc. (San Francisco, Calif.). For NMR measurements, the peptide concentration was typically ~2 mM in 0.6 mL of aqueous solution of 90% $H_2O$ and 10% $D_2O$ at pH 5.4. The pH of each sample was adjusted by using microliter aliquots of HCl or NaOH solution and measured directly in the 5-mm NMR tube with a micro-pH electrode (Wilmad-Labglass). The peptide/SDS molar ratio was 1:40, and the peptide/dioctanoyl phosphatidylglycerol (D8PG, Avanti Lipids) ratio was 1:5. These ratios were found to be sufficient for the peptides to adopt micelle-bound conformations.

All data were recorded on a four-channel Varian (Palo Alto, Calif.) INOVA 600 MHz NMR spectrometer equipped with a triple-resonance cryoprobe with a z-axis gradient. A set of 2D NMR spectra was collected for each peptide using States-TPPI at 25° C. In addition, data were also collected at 15° C. for the N-terminal fragment and at 35° C. for the C-terminal fragment of LL-37. NOESY spectra were acquired at a mixing time of 100 ms for peptide/micelle complexes (Jeener et al. (1979) J. Chem. Phys., 71:4546-4553). TOCSY experiments were performed with a mixing time of 75 ms using a clean MLEV-17 pulse sequence (Bax et al. (1985) J. Magn. Reson., 65:355-360; Griesinger et al. (1988) J. Am. Chem. Soc., 110:7870-7872). Two-dimensional homonuclear NMR spectra were collected with 512 increments (16-32 scans each) in t1 and 2K complex points in t2 time domains using a spectral width of 8510.6 Hz in both dimensions with the 1H carrier on water. In NOESY and TOCSY experiments, the water signal was suppressed by presaturation or WATERGATE (Piotto et al. (1992) J. Biomol. NMR, 2:661-665); for DQFCOSY32 experiments, water was suppressed by low power presaturation during relaxation delay (Rance et al. (1983) Biochem. Biophys. Res. Commun., 117:479-485).

Two 2D heteronuclear NMR spectra were recorded for each peptide at natural abundance using a gradient-enhanced version of HSQC experiments (Kay et al. (1992) J. Am. Chem. Soc., 114:10663-10665). For the $^1$H and $^{15}$N correlation, 30 increments (128 scans) were collected in the $^{15}$N dimension at a spectral width of 2200 Hz. For the $^1$H and $^{13}$C correlation, 80 increments (256 scans) were collected in the $^{13}$C dimension at a spectral width of 12,000 Hz. The data size in the proton dimension was 512 complex points. In these correlated spectra, the $^1$H, $^{15}$N, and $^{13}$C carriers were set at 4.77, 118.27, and 36.37 ppm, respectively.

All NMR data were processed on a Silicon Graphics Octane workstation (SGI) using the NMRPipe software (Delaglio et al. (1995) J. Biomol. NMR, 6:277-293). Time domain data were apodized by a 63° shifted squared sine-bell window function in both dimensions, zero-filled prior to Fourier transformation to yield a 2K×1K data matrix. To avoid the interaction of anionic 2,2-dimethylsilapentane-5-sulfonate sodium salt (DSS) with cationic peptides, the proton chemical shifts of the peptide were referenced to the water signal, which in turn was referenced to the methyl signal of internal DSS at 0.00 ppm (Keifer et al. (2004) Anal. Biochem., 331: 33-39; Wang et al. (2003) Protein Sci., 12:1087-1096). $^{15}$N and $^{13}$C chemical shifts were referenced based on the relative frequency ratios recommended by IUPAC (Markley, et al. (1998) J. Biomol. NMR, 12:1-23).

NMR data were analyzed using NMRDraw in the NMRPipe suite as well as PIPP (Delaglio et al. (1995) J. Biomol. NMR, 6:277-293; Garrett et al. (1991) J. Magn. Reson., 95:214-220). The peptide proton signals were assigned using the standard procedure based on 2D TOCSY, DQF-COSY, and NOESY spectra (Wuthrich, K. NMR of Proteins and Nucleic Acids; Wiley: New York, 1986). The $^{13}$Cα, $^{13}$Cβ, and $^{15}$N resonances for each peptide were assigned on the basis of the proton chemical shift assignments achieved above (Wang et al. (2006) Curr. Org. Chem., 10:569-581).

Structure Calculations. Three-dimensional structures of the peptides bound to deuterated SDS (Cambridge Isotope Laboratory) micelles at pH 5.4 and 25° C. were calculated based on both distance and angle restraints by using the simulated annealing protocol in Xplor-NIH (Schwieters et al. (2003) J. Magn. Reson., 160:65-73). The structure for the N-terminal fragment LL-37(1-12) was calculated using the 15° C. data due to a better NOESY spectrum. The distance restraints were obtained by classifying the NOE cross-peak volumes into strong (1.8-2.8 Å), medium (1.8-3.8 Å), weak (1.8-5.0 Å), and very weak (1.8-6.0 Å) ranges. The distance was calibrated on the basis of the typical NOE patterns in an α helix (Wuthrich, K. NMR of Proteins and Nucleic Acids; Wiley: New York, 1986). Peptide backbone restraints were obtained from the TALOS analysis of a set of heteronuclear chemical shifts, including $^1$Hα, $^{13}$Cα, $^{13}$Cβ, and $^{15}$N (Cornilescu et al. (1999) J. Biomol. NMR, 13:289-302). A broader range (up to 120°) than predicted was allowed for each angle in the structural calculations. In each case, a covalent peptide structure with random φ, ψ, and χ angles, but trans planar peptide bonds, was used as a starting structure. In total, 100 structures were calculated. An ensemble of 20 structures with the lowest total energy was chosen for structural analysis. This final ensemble of accepted structures satisfies the following criteria: no NOE violations greater than 0.5 Å, root-mean-square deviation (rmsd) for bond deviations from ideality less than 0.01 Å, and rmsd for angle deviations from ideality less than 5°.

The coordinates of the LL-37 core peptide and the N- and C-terminal fragments of LL-37 in SDS micelles have been deposited with the Protein Data Bank (PDB entries: 2FBS, 2FBU, and 2FCG).

Results

Identification of a Core Antibacterial and Anticancer Peptide from LL-37 by TOCSY-Trim and Activity Assays. Human LL-37 is a 37-residue peptide with a pair of leucines (LL) at the N-terminus. Its primary sequence is LLGDFFRK-SKEKIGKEFKRIVQRIKDFLRNLVPRTES (SEQ ID NO: 1) (Gudmundsson et al. (1996) Eur. J. Biochem., 238:325-332). Previous antibacterial assays using *Escherichia coli* D21 revealed MIC values in the range 5-25 μM (Johansson et al. (1998) J Biol. Chem., 273:3718-24; Oren et al. (1999) Biochem. J., 341:501-13). Using the wild type *E. coli* K12 strain, an MIC of 40 μM for LL-37 was determined. To narrow down the antibacterial region in LL-37, a series of peptides was designed (Table 1). Initially, LL-37 was cut into halves. The "cutting point" was chosen at the end of a string of six hydrophilic residues (underlined in the above sequence) and in the vicinity of G14 of the peptide. Hence, the N-terminal fragment corresponds to residues 1-12 of LL-37 (referred to as LL-37(1-12)), while the C-terminal fragment corresponds to residues 13-37 (referred to as LL-37(13-37)). Antibacterial and anticancer assays showed that the N-terminal fragment was not active, while the C-terminal fragment had toxic effects on drug-resistant KBv and drug-sensitive KB cancer cells as well as *E. coli* (Table 2).

TABLE 1

Name, Sequences, and HPLC Retention Times of Peptides.

| Peptide | Sequence | SEQ ID NO | $t^{RP}$ (min)[a] |
|---|---|---|---|
| LL-37(1-12) | LLGDFFRKSKEK | 2 | 26.6 |
| LL-37(13-37) | IGKEFKRIVQRIKDFLRNLVPRTES | 3 | 39.8 |
| LL-37(17-32)[b] | FKRIVQRIKDFLRNLV | 4 | 42.0 |
| LL-37(17-29) | FKRIVQRIKDFLR | 5 | 37.2 |
| LL-37 (1-4, 17-27) | LLGDFKRIVQRIKDF | 6 | 32.8 |
| dLL-37(17-32)[c] | FKRIVQRIKDFLRNLV | 7 | 29.8 |
| aurein 1.2 | GLFDIIKKIAESF | 8 | 42.0 |
| anchor[d] | GLFDKLKSLVSDDKK | 9 | 29.5 |

[a]Retention time of the peptide (in minutes) on a reversed-phase HPLC column as a measure of hydrophobicity (Chen et al. (2005) J. Biol. Chem., 280:12316-12329; Kim et al. (2005) J. Peptides, 26:2050-2056).
[b]Several peptides, including LL-37(17-29), LL-37(17-32), dLL-37(17-32), and LL-37(1-4,17-27), were amidated at the C-terminus to improve the stability of the peptides.
[c]Residues I20, I24, and L28 of this peptide are D-amino acids (bold and underlined).
[d]The bacterial membrane anchor of glucose-specific enzyme IIA$^{Glc}$ of *E. coli* (Wang et al. (2000) J. Biol. Chem., 275:39811-39814).

TABLE 2

Antibacterial and Anticancer Activity of LL-37 Fragments.

| Peptide | E. Coli MIC[a] (μM) | KBv LC$_{50}$[b] (μM) | KB LC$_{50}$ (μM) | HBMEC LC$_{50}$ (μM) |
|---|---|---|---|---|
| LL-37(1-12) | NE[c] | NE | NE | NE |
| LL-37(13-37) | 80 | 39 ± 0 | 40 ± 0 | 38 ± 3 |
| LL-37(17-32) | 20 | 30 ± 0 | 30 ± 1 | 25 ± 1 |
| LL-37(17-29) | 40 | 60 ± 0 | 57 ± 3 | 55 ± 2 |
| LL-37(1-4, 17-27) | 250 | NE | NE | NE |
| dLL-37(17-32)[d] | 40 | NE | NE | NE |

[a]Minimum inhibitory concentration measured as described in Methods. The peptides were quantified using the method of Waddell (Waddell, W. J. (1956) J. Lab. Clin. Med., 48:311-314). In this method, the peptide concentration (in mg/mL) is calculated by using the difference in UV absorbance at 215 and 225 nm multiplied by 0.144.
[b]The peptide concentration that kills 50% of the cells.
[c]"NE" stands for no toxic effect.
[d]This D-peptide analogue contains an additional glycine at the N-terminus. It has identical antibacterial activity to that of its corresponding L-diastereomer (i.e., consisting of all L-amino acids).

In light of these observations, a third peptide was created based on the TOCSY spectrum of LL-37(13-37) by trimming off disordered regions (FIG. 1A). In the TOCSY spectrum, the structured portion of a peptide, due to association with micelle, gives very weak or no cross-peaks from the backbone amide protons to side chains, whereas those disordered peptide regions or weakly micelle-binding regions display intense crosspeaks (Wang, et al. (2003) Protein Sci., 12:1087-1096; Wang et al. (1996) J. Biochemistry, 35:10358-10366; Wang et al. (1997) J. Biochemistry, 36, 13657-13666). In FIG. 1A, strong TOCSY patterns for residues 30-32 and 34-37 were labeled. Further, two or more sets of intense cross-peaks were observed for residue G14, E16, T35, E36, and S37, indicating multiple conformations. The crosspeaks for other residues of the peptide were barely visible. As a consequence, a third peptide, LL-37(17-32), was obtained by removing nonessential micelle-binding residues 13-16 as well as 33-37 from LL-37(13-37). Antibacterial and anticancer assays found that LL-37(17-32) was more active than LL-37(13-37).

The peptide was further shortened based on the TOCSY spectrum of LL-37(17-32) in SDS micelles (FIG. 1B). Clearly, side-chain peak intensities for residues N30, L31, and V32 were much stronger than those for residues 17-29. Note that N30, L31, and V32 also gave strong TOCSY relays in FIG. 1A, indicating that the flexibility of these residues was inherent and not a result of peptide truncation. Therefore, residues 30-32 were also deleted, leading to a fourth peptide LL-37(17-29) of only 13 residues. Compared to LL-37(17-32), both the antibacterial and anticancer activities of LL-37-(17-29) were reduced (Table 2). These results suggest that residues N30-V32 play a role in determining the cytotoxic effects of LL-37. In the two cancer cell lines and one normal human cell line tested, these LL-37 fragments showed no cell selectivity, consistent with the previous observations that LL-37 is toxic to human cells (Johansson et al. (1998) J. Biol. Chem., 273, 3718-24; Oren et al. (1999) Biochem. J., 341: 501-13).

To design a miniature version of LL-37, L28R29 from LL-37(17-29) was removed and residues 1-4 were added to the N-terminus. The resultant peptide, LL-37(1-4, 17-27), nevertheless, is largely no longer active. These particular studies emphasize the importance of residues L28R29 for both antimicrobial and anticancer cytotoxic effects of the peptide.

Other laboratories also found or designed a variety of LL-37 fragments using different strategies. Using V8 proteinase hydrolysis, Sieprawska-Lupa et al. found LL-37(17-37) is as active as the intact molecule against Staphylococcus aureus (Sieprawska-Lupa et al. (2004) Antimicrob. Agents Chemother., 48:4673-4679). Likewise, Nagaoka et al. improved the lipopolysaccharide-neutralizing ability of LL-37(15-32) by site-directed mutagenesis (Nagaoka et al. (2002) Clin. Diagn. Lab Immunol., 9:972-982). Using a synthetic peptide library of LL-37, Gallo and colleagues found LL-37(11-30) with a broad spectrum of antimicrobial activity (Braff et al. (2005) J Immunol., 174:4271-4278). A recent paper systematically scanned LL-37 by synthesizing numerous 22mers (Nell et al. (2006) J. Peptides, 27:649-660). LL-37(14-36) was chosen and further modified by site-directed mutagenesis. Interestingly, all these active peptides contain the essential segment corresponding to residues 17-29 of LL-37, which was found by TOCSY-trim (FIG. 1ABC). Because LL-37(17-29) is the shortest antimicrobial and anticancer peptide identified to date, this segment may be referred to as the LL-37 core peptide.

Structure of the LL-37 Core Peptide. To further understand the antibacterial activity of the LL-37 core peptide, its 3D structure in detergent micelles was determined by the established 2D NMR approach (Wuthrich, K. NMR of Proteins and Nucleic Acids; Wiley: New York, 1986). Because the major anionic lipids in bacteria are phosphatidylglycerols (PGs), short chain PGs have been used for structural determination of antimicrobial peptides by liquid-state NMR (Keifer et al. (2004) Anal. Biochem., 331:33-39; Wang et al. (2003) Protein Sci., 12:1087-1096; Wang et al. (2004) Spectroscopy, 18:257-264). Thus, the NOESY spectra for the LL-37 core peptide were collected in D8PG micelles. As a comparison, the Hα chemical shifts for the LL-37 core peptide in D8PG and SDS micelles are presented in FIG. 2A. The two curves superimposed nicely. Further, there were similar NOE contacts between the hydrophobic side chains of F27 and L28 as well as F17 and V21 in both micelles. These results indicate that the LL-37 core peptide possesses similar structures in the two environments. Nearly identical structures in these two environments were also found previously for both aurein 1.223 and a bacterial membrane anchor (Wang et al. (2003) Protein Sci., 12:1087-1096). Interestingly, molecular dynamics simulations found that the structure of gramicidin A determined in SDS micelles better represents the structure elucidated in lipid bilayers (Allen et al. (2003) J. Am. Chem. Soc., 125:9868-9877). All these data would imply that detergent micelles mimic membrane environments well.

Because of the chemical shift similarities of the LL-37 core peptide in SDS and D8PG (FIG. 2A), deuterated SDS micelles was used for 3D structure determination of the LL-37 core peptide for the best quality, as deuterated D8PG is not yet commercially available. In total, 156 distance restraints were used in the structural calculations (Table 3). The distance-based structure was refined by natural abundance heteronuclear chemical shifts ($^1$Hα, $^{13}$Cα, $^{13}$Cβ, and $^{15}$N), because scalar coupling data are difficult to measure for micelle-bound peptides due to line broadening (Henry et al. (1994) Methods Enzymol., 239:515-535; Opella et al. (2004) Chem. Rev., 104:3587-3606; Wang et al. (2005) 280:5803-5811). Based on these chemical shifts, peptide backbone angles (φ, ψ) for residues 18-28 were derived from TALOS (Cornilescu et al. (1999) J. Biomol. NMR, 13:289-302). Inclusion of these angle restraints led to an excellent Ramachandran plot with 100% of backbone angles of the peptide in the most favored region. Previous studies indicate that, in the absence of angle restraints, such a good geometry may not be obtained especially when the distance restraints are not sufficient (Wang et al. (2005) J. Biol. Chem., 280:5803-5811). The rmsd for superimposing backbone atoms of residues 18-28 of the core peptide was 0.32 Å, indicative of a good precision. As shown in FIG. 3A, the LL-37 core peptide adopts an amphipathic helical structure. The side chains of residues F17, I20, V21, I24, F27, and L28 are located on the hydrophobic surface, whereas the side chains of residues K18, R19, Q22, R23, D27, and R29 are located on the hydrophilic surface. The amphipathic nature of the structure can also be seen from the potential surface (FIG. 4A), where positively and negatively charged side chains are in light gray and dark gray, respectively. Such a structural feature is ideal for targeting negatively charged bacterial membranes.

TABLE 3

Structural Statistics of LL-37 Fragments

| Peptide region | Distance restraints | Backbone angles | Superimposed region | Backbone msd (Å) | Helical region |
|---|---|---|---|---|---|
| 1-12 | 68 | 10 | 3-7 | 0.29 | 3-7 |
| 13-37 | 165 | 28 | 17-30 | 0.34 | 17-30 |
| 17-29 | 156 | 22 | 18-28 | 0.32 | 18-28 |
| 17-32 | 241 | none | 19-30 | 0.65 | 28-31 |

Comparison of the LL-37 Core Peptide with the Bacterial Membrane Anchor and Aurein 1.2. The positioning of the two aromatic rings in the structure of the LL-37 core peptide is reminiscent of that observed previously in aurein 1.2 (Table 1), an antimicrobial and anticancer peptide isolated from the Australian Bell Frog (Rozek et al. (2000) J. Eur. J. Biochem., 267:5330-5341). The two aromatic rings in either peptide show contacts with adjacent hydrophobic side chains, forming hydrophobic clusters for membrane binding (FIGS. 3A and B). In the case of aurein 1.2, an alteration of F13 to isoleucine abolished anticancer activity of the peptide (Rozek et al. (2000) J. Eur. J. Biochem., 267:5330-5341). Alternatively, changing D13 of the nontoxic bacterial membrane anchor (FIG. 3C) to F13 converted the nontoxic membrane anchor to an antibacterial peptide (Wang et al. (2005) J. Biol. Chem., 280:5803-5811). In the case of the LL-37 core peptide, further removal of L28R29 caused a significant reduction in antibacterial activity and a loss in anticancer activity (Table 2). According to the 3D structure in FIG. 3A, removal of L28 would disrupt the hydrophobic packing between F27 and L28. All these results indicate the importance of the aromatic-ring-involved hydrophobic clusters for membrane binding (Wang et al. (1996) J. Biochemistry, 35:10358-10366.).

Figure 3:
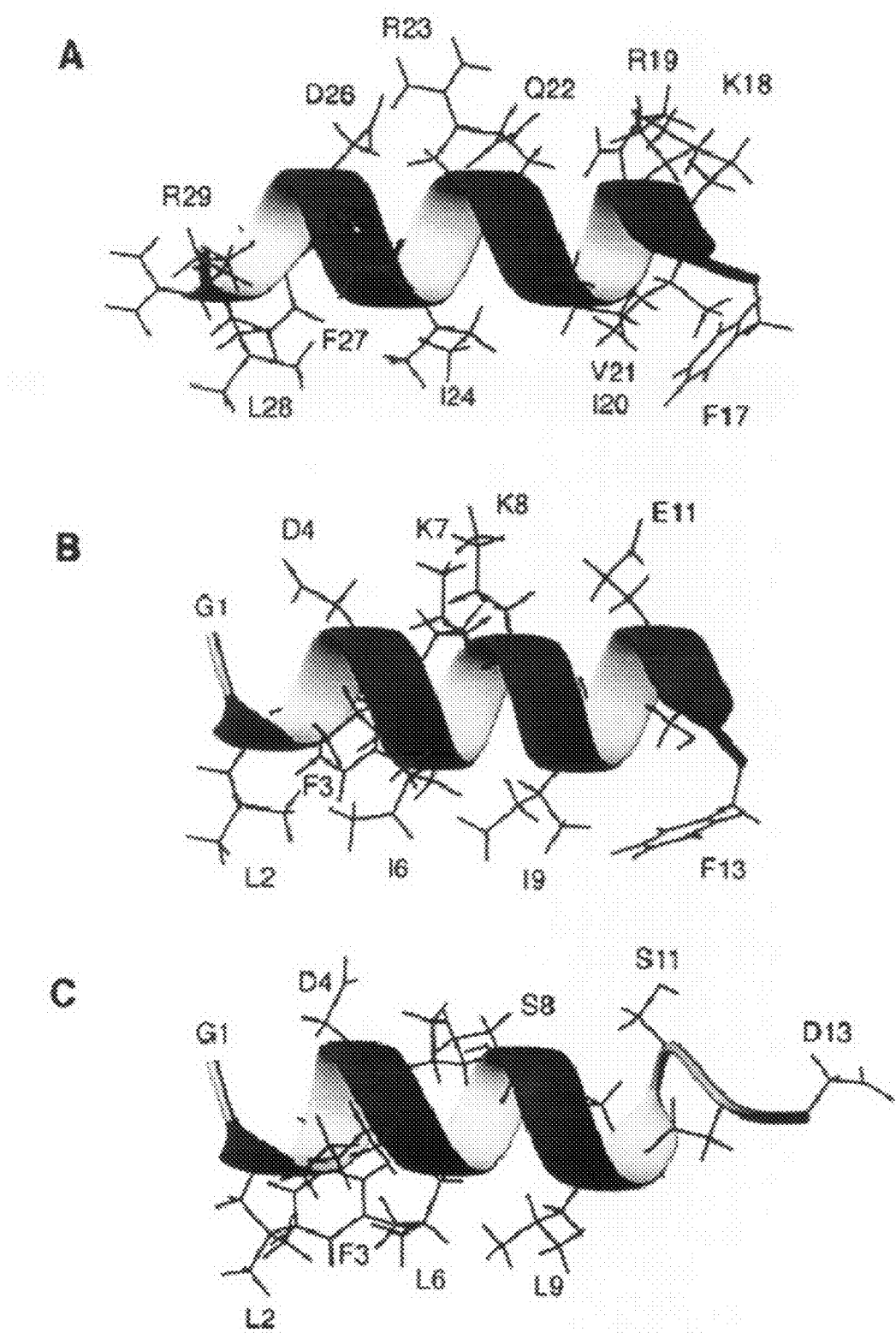

In terms of inhibiting the growth of E. coli, the LL-37 core peptide (MIC 40 μM) is more active than aurein 1.2 (MIC 75 μM; Wang et al. (2005) J. Biol. Chem., 280:5803-5811). Because these two peptides possess the same backbone structure and equivalent hydrophobic clusters (FIG. 3), the difference in activity may be determined by the additional number of cationic side chains in the LL-37 fragment. Indeed, there are five cationic side chains in the LL-37 core peptide (K18, R19, R23, K25, and R29) but only two in aurein 1.2 (K7 and K8). In the case of aurein 1.2 and the bacterial membrane anchor, both peptides have two cationic side chains in the membrane-targeting helical domain (FIGS. 3B and C). The toxic effect of aurein 1.2 on both bacterial and cancer cells was previously ascribed to its broader and longer hydrophobic surface (FIG. 4B; Wang et al. (2005) J. Biol. Chem., 280:5803-5811; Rozek et al. (2000) J. Eur. J. Biochem., 267:5330-5341). In contrast, the absence of cytotoxicity of the bacterial membrane anchor is determined by the short and narrow hydrophobic surface (FIG. 4C). The broader hydrophobic surface of aurein 1.2 versus that of the bacterial membrane anchor enabled the former to effectively penetrate into and perturb the bacterial membranes. Thus, increase in either the number of cationic charges or hydrophobicity enhances the cytoxicity of the peptide.

Figure 5:
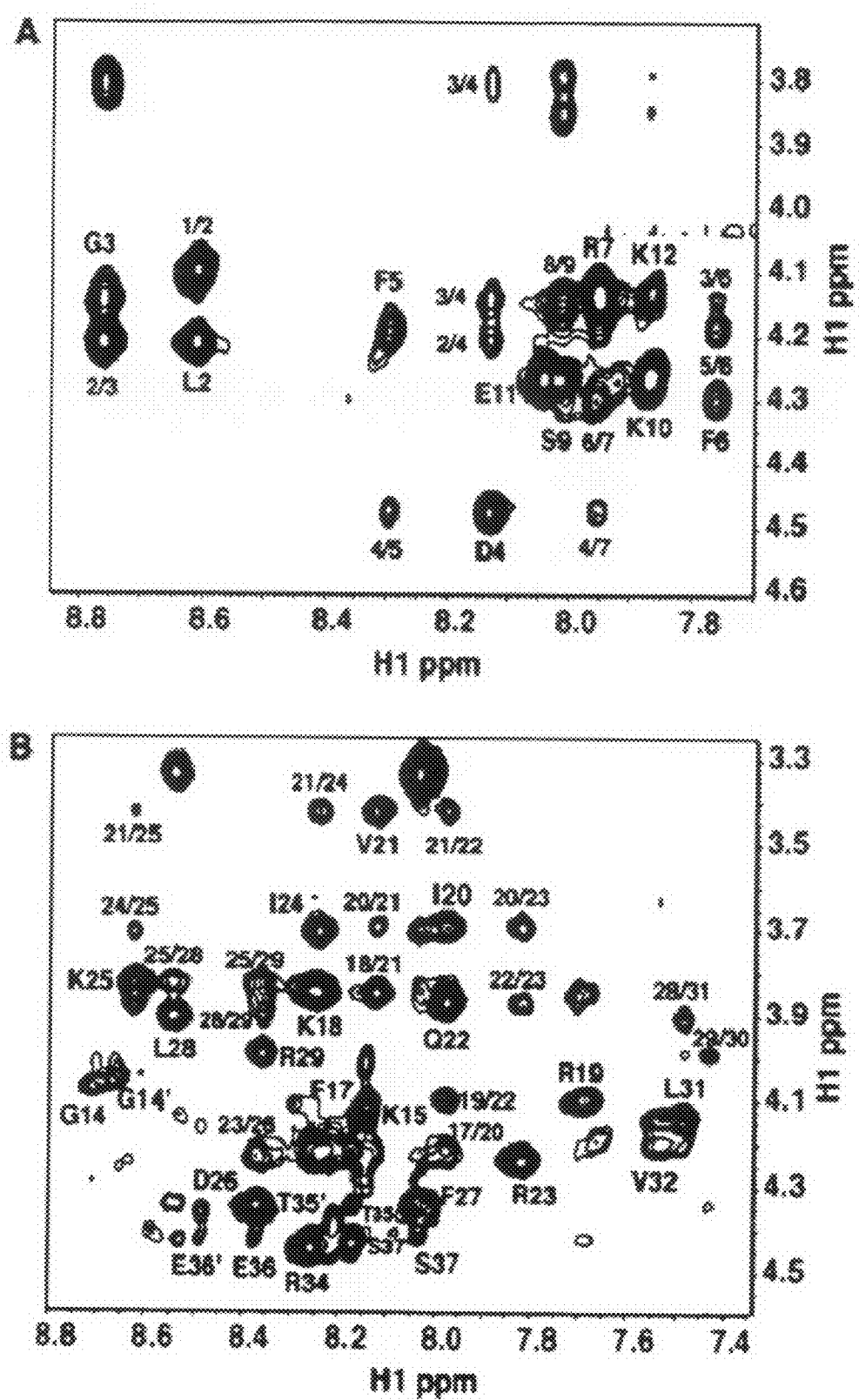

Structures of the N- and C-Terminal Fragments of LL-37. Because LL-37 can be cleaved in vivo into similar fragments, the structures of both LL-37(1-12) and LL-37(13-37) was also determined in SDS micelles for a better understanding of the structure-activity relationship (Murakami et al. (2004) J Immunol., 172:3070-3077). To illustrate the quality of the data, FIG. 5 shows a portion of the NOESY spectra for both the N-(A) and C-terminal (B) peptides. As labeled in the spectra of the C-terminal peptide LL-37(13-37), the (i, i+3) type of NOE cross-peaks covers residues 17-31, indicating a helical structure for that region. The NOE crosspeak from the Hα of V32 to the Hδ of P33 indicates a trans conformation for the proline in LL-37(13-37). As described above, solution structures of the LL-37 fragments were determined based on both distance and angle restraints. In total, 68 and 165 distance restraints were found for the N- and C-terminal fragments, respectively. Based on natural abundance chemical shifts (Wang et al. (2005) J. Biol. Chem., 280:5803-5811), the backbone angles (φ and ψ) for residues 3-7 of the N-terminal fragment and residues 17-29 of the C-terminal fragment of LL-37 were restrained in the helical region (Table 3).

According to the MOLMOL analysis (Koradi et al. (1996) J. Mol. Graphics, 14:51-55), the majority of the structures showed a helical structure in the region corresponding to residues 17-30 (FIG. 6A). When the backbone atoms of residues 17-30 were superimposed, the rmsd was 0.34 Å relative to the mean structure. The backbone rmsd increased dramatically to 2.3-2.7 Å, however, when the superimposed region was expanded to include either residues 13-16 or 32-37. An investigation of the NOE list revealed that the number of NOE cross-peaks for those regions was less than 3 per residue, while the average number of NOEs for residues 17-31 was 10. Such an NOE distribution along the polypeptide chain is consistent with the structure in FIG. 6A, where the central portion is well defined with both ends "frayed". It is likely that those poorly defined peptide regions do not or weakly interact with the micelles (Wang et al. (2003) Protein Sci., 12:1087-1096; Wang et al. (1996) J. Biochemistry, 35:10358-10366).

Figure 1C:
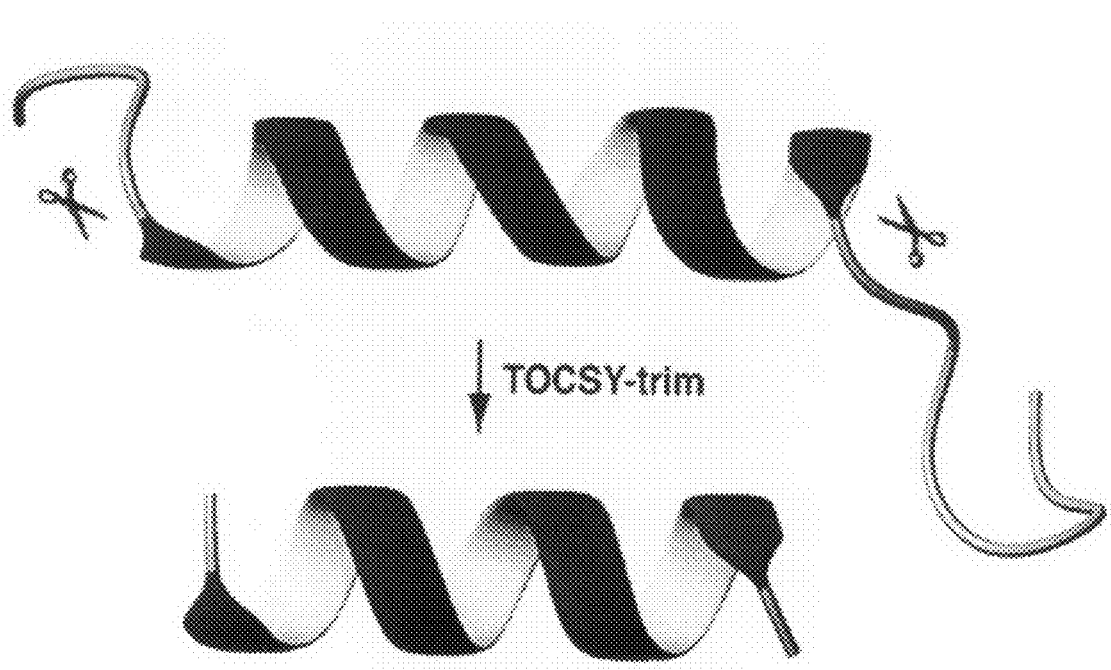

Interestingly, the well-defined helical region in the C-terminal fragment of LL-37 (FIG. 6B) corresponds nicely to the LL-37 core peptide (FIG. 3A) identified by TOCSY-trim (FIG. 1). Thus, a core antimicrobial peptide would also have been found in the C-terminal fragment of LL-37 based on structural determination. Further, TALOS analysis of a set of $^1H$, $^{13}C$, and $^{15}N$ chemical shifts of LL-37(13-37) also indicates that residues 17-29 are helical (Cornilescu et al. (1999) J. Biomol. NMR, 13:289-302). The agreement of TOCSY-trim with both TALOS analysis and structure determination further supports the usefulness of TOCSY-trim in identifying a core membrane-targeting peptide embedded in a longer sequence. The advantage of TOCSY-trim is that a membrane-binding peptide region could be mapped prior to the completion of 3D structure determination, which usually takes a longer time and more efforts. Herein, LL-37 and its fragments were chemically synthesized at natural abundance and proton-based TOCSY spectra were employed (FIG. 1). When LL-37 is isotopically labeled, for example, by using a bacterial system, other NMR techniques such as heteronuclear NOE experiments (small or negative NOEs for flexible regions) and a carbon version TOCSY (strong cross-peaks as in the proton version) could also be applied in identifying minimal membrane-targeting regions.

The antibacterial activity of the LL-37 core peptide is comparable to the longer LL-37 fragments (Table 2). The slightly lower activity of LL-37(13-37) may result from the interference of the disordered regions with membrane binding of the peptide (FIGS. 6A and B). It also suggests that only cationic and hydrophobic side chains in the membrane-targeting domains contribute to the antibacterial activity of the peptide. In terms of anticancer activity, LL-37(17-29) became slightly less active than the longer ones, indicating that the truncated hydrophobic residues L31 and V32 also play a role in interaction with human cells. The decrease in hydrophobicity of LL-37(17-29), compared to either LL-37 (17-32) or LL-37(13-37), is supported by the slightly shorter retention time on the reversed-phase HPLC column (Table 1).

The structure of the N-terminal peptide LL-37(1-12) is displayed in FIG. 6C. Only a one-turn helix covering residues 3-7 was found. The rmsd for superimposing the helical region was 0.29 Å (Table 3). According to the Ramachandran plot, 62%, 18%, 18%, and 2% of the backbone angles for the N-terminal peptide are located in the most favored, additionally allowed, generously allowed, and disallowed regions, respectively. A similar distribution (76%, 15%, 7%, and 2%) was observed for the C-terminal fragment LL-37(13-37). These plots differ from that of the LL-37 core peptide, where 100% of the backbone angles are in the most favored region of the Ramachandran plot. A detailed residue-by-residue analysis found that nearly all residues not located in the most favored regions are those in the poorly defined peptide regions, that is, residues 8-12 in the case of LL-37(1-12) and residues 13-16 as well as 31-37 in the case of LL-37(13-37).

In FIG. 6C, the aromatic rings of F5 and F6 are perpendicular to each other and packing with the side chain of L2, forming one single hydrophobic cluster. Such an orientation between the aromatic rings of F5 and F6 offers an explanation for the upfield chemical shift of the Hδ protons of F5 at 6.85 ppm (FIG. 7A) as a result of the ring current effect of F6. The single hydrophobic cluster in this peptide is responsible for the shortest retention time on the reversed-phase HPLC column (see Table 1). The poor hydrophobicity of the peptide may also be the reason, at least in part, for the lack of antibacterial or anticancer activity. Since aromatic-aromatic interactions play a significant role in stabilizing protein structure (Burley et al. (1985) Science, 229:23-28.), in binding to lipids (Wang et al. (1996) J. Biochemistry, 35:10358-10366), and in stabilizing the lipid-free oligomeric structure (Wang, G. (2002) FEBS Lett., 529:157-161), aromatic-aromatic interactions between F5 and F6 may be essential for oligomerization of LL-37 observed previously (Johansson et al. (1998) J Biol. Chem., 273:3718-24; Oren et al. (1999) Biochem. J., 341:501-13.).

Figure 7:
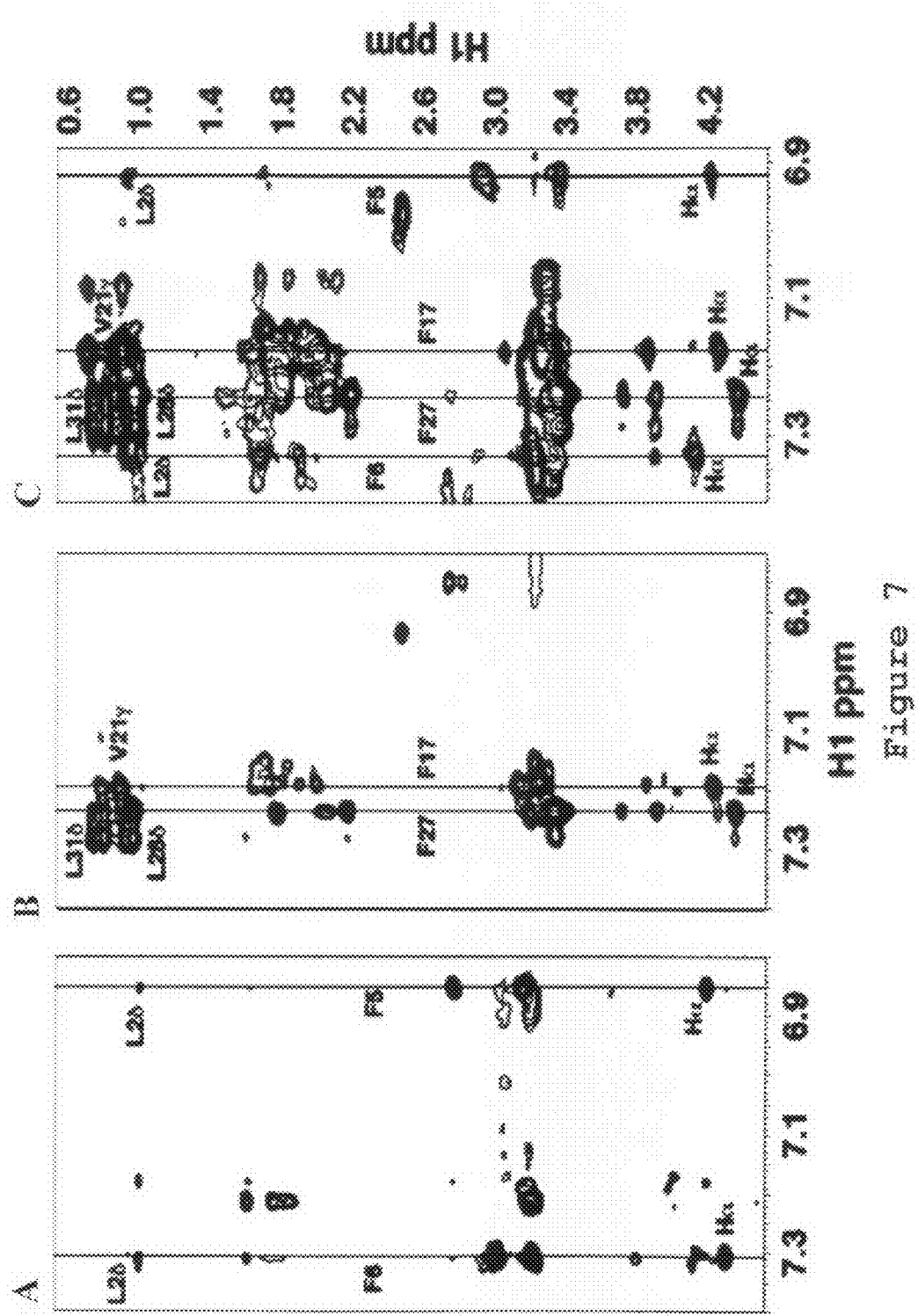

Peptide-Aided Signal Assignments of Intact LL-37. As shown above, the structure of the LL-37 core peptide (FIG. 3A) is retained in the C-terminal fragment LL-37(13-37) (FIG. 6B) as well. Correspondingly, the Hα chemical shift plots for residues 17-29 in the core peptide as well as in LL-37(13-37) against residue number are remarkably similar (FIG. 2B). Spectral identities between the fragments and intact LL-37 could be seen. The sparse signal regions allowed for the use of the peptide-aided signal assignment approach for partial assignments (Wang et al. (1997) J. Biochemistry, 36:13657-13666). For example, the Hα of V21 in LL-37 is well resolved. Its chemical shift at 3.40 ppm is identical to those in the LL-37 core peptide (3.41 ppm) and the C-terminal fragment (3.43 ppm). FIG. 7A shows the aromatic regions of the NOESY spectra of LL-37(1-12) (panel A), LL-37(13-37) (B), and LL-37 (C). Indeed, the chemical shifts of the Hδ protons of F5 and F6 at 6.85 and 7.31 ppm in the spectrum of LL-37(1-12) are very similar to 6.92 and 7.33 ppm in the spectrum of LL-37. Likewise, the chemical shifts of the Hδ protons of F17 and F27 in the C-terminal fragment (at 7.19 and 7.24 ppm) are nearly identical to those in LL-37 (at 7.18 and 7.24 ppm). Further, there are similar hydrophobic interactions between the aromatic rings and hydrophobic side chains ranging from fragments to intact LL-37 (see FIG. 7). Finally, strong TOCSY relays observed for residues 34-37 in LL-37(13-37) (FIG. 1) were also found in intact LL-37. Thus, the structures found in the fragments might also exist in intact LL-37. It may be proposed that a structural model for this important human defense molecule, which consists of two amphipathic helices connected by a yet-to-be-defined linker in the vicinity of G14.

Structure of a D-Amino Acid Containing Peptide Analogue of LL-37(17-32). Previous (Johansson et al. (1998) J Biol. Chem., 273:3718-24; Oren, et al. (1999) Biochem. J., 341:501-13) and current studies indicate that LL-37 and its fragments showed poor cell selectivity (Table 2). As the only antibacterial cathelicidin peptide in humans, there is high interest in exploiting LL-37 as a template to design novel antimicrobial peptides (Wang, G. (2006) Curr. Org. Chem., 10:569-581; Schwieters et al. (2003) J. Magn. Reson., 160:65-73; Cornilescu et al. (1999) J. Biomol. NMR, 13:289-302). The toxicity of LL-37-derived peptides to human cells must be abolished. For this purpose, D-amino acids may be incorporated into the peptide. Shai and colleagues found that incorporation of D-amino acids at every 2-3 residues is effective in disrupting helical structures (Papo et al. (2004) Biochemistry, 43:6393-6403). Because LL-37(17-32) showed the highest cytotoxic effects on both bacteria and cancer cells (Table 2), it was chosen as a peptide template. Residues I20, I24, and L28 of LL-37(17-32) were replaced by their corresponding D-amino acids. The resultant peptide is referred to as dLL-37(17-32) (Table 1). Antibacterial assays found that this D-amino acid containing peptide retained the same activity as that of LL-37(17-32). Interestingly, dLL-37(17-32) was toxic to neither cancer cells nor normal human cells (Table 2). D-Amino acid incorporation has been previously applied to pardaxin, melittin, and other peptides leading to D-peptide analogues with similar antibacterial activities but no cytotoxic effects on mammalian cells (Shai et al. (1996) J. Biol. Chem., 271:7305-7308; Oren et al. (1996) Biochemistry, 36:1826-1835; Oren et al. (2002) Eur. J. Biochem., 269:3869-3880; Chen et al. (2005) J. Biol. Chem., 280:12316-12329).

To provide insight into the structural basis for the detoxification of the LL-37 peptide by D-amino acid incorporation, a structural study of dLL-37(17-32) bound to SDS micelles was also performed. The fingerprint region of the NOESY spectrum of this D-amino acid containing peptide is given in FIG. 8A. The NOE contacts between adjacent residues, viz., of (i, i+1) type, are strong, and there are only very few and weak (i, i+2) or (i, i+3) types of NOEs and no (i, i+4) type of NOEs. Such an NOE pattern (e.g., FIG. 5B) differs from that observed for the corresponding peptide consisting of all L-amino acids (L-diastereomer), indicating a successful disruption of the canonical α helical structure. Because of a new type of 3D structure, the NOE assignments of dLL-37(17-32)

were performed in an iterative manner by starting from those with unique chemical shifts. In total, 241 NOE cross-peaks were used for structural calculation. When TALOS (Cornilescu et al. (1999) J. Biomol. NMR, 13:289-302) was applied to the analysis of the heteronuclear chemical shifts of the peptide, only residues F27, R29, and N30 were predicted in the helical region. Because of the lack of D-amino acid data in the TALOS program, the results were not included in the structural refinement. A backbone view of the structural ensemble of dLL-37(17-32) is provided in FIG. 8B. The rmsd was 0.65 Å when the backbone atoms of residues 19-30 were superimposed.

At the N-terminus, the structure of dLL-37(17-32) consists of multiple turns, which may be referred to as an omega-turn, due to a shape similar to the letter ω after a 180° flip of FIG. 9A. The C-terminal region, residues 28-31, forms a 310 helix according to MOLMOL analysis (Koradi et al. (1996) J. Mol. Graphics, 14:51-55). The aromatic ring of F27 shows hydrophobic contacts to I24, L28, and L31. Similarly, there are interactions from F17 to I20 and V21. These NOE contacts directly bring together the hydrophobic side chains, leading to a new amphipathic structure with a distorted backbone structure (FIG. 9A).

Because both dLL-37(17-32) (FIG. 9B) and LL-37(17-32) (FIG. 9C) adopt an amphipathic structure with five positively charged side chains on the hydrophilic surface, they should possess an identical positive membrane perturbation potential when attacking the negatively charged bacterial membranes in terms of electrostatic interactions. The identical antibacterial activity of the D- and L-form peptides suggest that electrostatic interactions dominate. The hydrophobic part, however, may have determined their toxic differences to human cells (Table 2). One of the current approaches for quantifying the hydrophobicity of peptides is to use the retention time on a reversed-phase HPLC (Chen et al. (2005) J. Biol. Chem., 280:12316-12329; Kim et al. (2005) J. Peptides, 26:2050-2056). The retention times of LL-37(17-32) and dLL-37(17-32) are 42 and 29.8 minutes, respectively, indicating that the latter is much less hydrophobic than the former. Structurally, a clear defect (under residue R19 in FIG. 9B) could be seen on the hydrophobic surface of dLL-37(17-32). This was caused primarily by the deviations of I20 and V21 from the hydrophobic surface. In other words, the distortion of the peptide backbone conformation by D-amino acids caused an out-of-phase packing between the two hydrophobic clusters involving aromatic phenylalanines (FIG. 9A). As a comparison, the hydrophobic side chains in the structure of the same peptide region, consisting of L-amino acids, all pack in-phase to form a single coherent hydrophobic surface (FIGS. 6B and 9C). The hydrophobic defects in FIG. 9B may provide a structural basis for the poor hydrophobicity of this D-amino acid containing peptide.

To provide additional insight into the basis for cell selectivity, dLL-37(17-32) was compared with the bacterial membrane anchor (Wang et al. (2000) J. Biol. Chem., 275:39811-39814). Inasmuch as the nontoxic bacterial membrane anchor (FIGS. 2C and 3C) interacts with anionic lipids but not with zwitterionic lipids, it is proposed that its hydrophobic surface contains the minimal requirement for bacterial membrane targeting (Wang et al. (2000) J. Biol. Chem., 275:39811-39814; Wang et al. (2005) J. Biol. Chem., 280:5803-5811). The retention time of the bacterial membrane anchor was found to be 29.5 minutes, which is essentially identical to that of dLL-37(17-32) (Table 1). In analog to the bacterial membrane anchor, one would predict that dLL-37(17-32) does not bind to the membranes of human cells rich in zwitterionic lipids. This would appear to be the case as dLL-37(17-32) lost its toxicity to human brain endothelial cells as well as cancer cells (Table 2). Since a reduced hydrophobicity after introducing D-amino acids was also observed for other peptides, it may be the case that the incoherent hydrophobic packing offers a useful interpretation at the structural level for D-amino acid detoxification (Chen et al. (2005) J. Biol. Chem., 280:12316-12329; Rosenfeld et al. (2005) J. Biol. Chem., 281:1636-1643).

EXAMPLE 2

Aurein 1.2 is an antimicrobial and anticancer peptide isolated from an Australian frog. Aurein 1.2 can be considered a model peptide for the following two reasons. First, aurein 1.2, from the Australian Bell Frog *Lithoria aurea* shows sequence homology to the membrane anchor (15 residues at the N-terminus, see Table 4) of the glucose-specific enzyme IIA from *Escherichia coli* (Rozek et al. (2000) Eur. J. Biochem., 267: 5330-5341; Wang et al. (2000) J. Biol. Chem., 275:39811-39814; Wang et al. (2005) J. Biol. Chem., 280:5803-5811). Second, aurein 1.2 also shows sequence homology to a portion of the peptide sequence of human LL-37. The spacing between F17 and F27 in human LL-37 is identical to that between F3 and F13 in aurein 1.2. Further, a greater sequence similarity was achieved by reversing the sequence of the segment corresponding to residues 17-29 of LL-37 (see Table 4 wherein identical residues are bolded and semi-conserved residues relative to aurein 1.2 are underlined). This LL-37-derived aurein 1.2 analog is hereinafter referred to as LLAA (Table 4). Herein, the three-dimensional structure of LLAA is provided along with its interaction with dioctanoyl phosphatidylglycerol (D8PG). The sequence similarities, ranging from the bacterial membrane anchor, to an amphibian antimicrobial peptide, to a peptide derived from human LL-37, allow for a better understanding of the differences in the antibacterial activity of these peptides.

TABLE 4

Peptide sequences, properties, and antibacterial activity of aurein 1.2 analogs.

| Peptide | Amino Acid Sequence | # of K/R | $t_{RP}{}^a$ (min) | % Helix$^b$ | MIC$^c$ (μM) | SEQ ID NO: |
|---|---|---|---|---|---|---|
| LLAA | RLFDKIRQVIRKF | 5 | 30.8 | 97 | 20 | 12 |
| Aurein 1.2 | GLFDIIKKIAESF | 2 | 43.0 | 95 | 75 | 13 |
| F13X-aurein 1.2 | GLFDIIKKIAESX | 2 | 38.3 | 100 | 160 | 14 |
| F13W-aurein 1.2 | GLFDIIKKIAESW | 2 | 40.5 | 97 | 320 | 15 |
| Membrane Anchor | GLFDKLKSLVS-DDKK | 4 | 29.5 | 64 | inactive | 16 |

$^a$Retention time on a reverse-phase column of HPLC as a measure of hydrophobicity (Kim et al. (2005) Peptides, 26: 2050-2056; Chen et al. (2005) J. Biol. Chem., 280: 12316-12329).
$^b$Helix percentage was calculated based on the average Hα secondary shifts of the peptide divided by 0.35 (Rizo et al. (1993) Biochemistry, 32: 4881-4894). The data for the bacterial membrane anchor and aurein 1.2 were taken from Wang et al. (J. Biol. Chem. (2005) 280: 5803-5811). For the F13X mutant, the helicity was found to be 115%. This helicity offshoot may be attributed to the ring current effect. Assuming the ring current effect of X13 caused an upfield shift of 0.7 ppm for the Hα of A10, the helicity is reduced to 100%. Thus, the helicity of the F13X mutant in this Table should be treated as an estimation.
$^c$Minimum concentration at which *E. coli* growth is completely inhibited. The bacterial membrane anchor is not toxic at the highest concentration used (0.32 mM; Wang et al. (2005) J. Biol. Chem., 280: 5803-5811). The peptides were quantified by Waddell's method (Waddell, W. J. (1956) J. Lab. Clin. Med., 48: 311-314). In this method, the peptide concentration (in mg/ml) was estimated based on the difference in UV absorbance at 215 and 225 nm multiplied by 0.144.

Materials and Methods

Materials. All peptides (>95% purity) were synthesized and purified by Genemed Synthesis (San Francisco, Calif.). Deuterated SDS (>99%) was obtained from Cambridge Isotope Laboratories (Andover, Mass.). Protonated D8PG (>98%) was purchased from Avanti Polar Lipids (Alabaster, Ala.). Chloroform was removed from phospholipids under a stream of nitrogen gas followed by evaporation under vacuum overnight. D8PG and SDS were used without further purification.

Antibacterial assay. The antibacterial activity of the peptides was analyzed using the standard microdilution approach (Wang et al. (2005) J. Biol. Chem., 280:5803-5811). In brief, a small culture of E. coli strain K12 3000 was grown overnight. A fresh culture was inoculated with a small aliquot of the overnight culture and incubated at 37° C. until the culture reached the logarithmic stage (A600 ~0.5, 9×10$^8$ cells/ml). The culture was then diluted to A600 ~0.001 and partitioned into a 96-well plate with ~10$^6$ cells per well (90 µl each). Then, 10 µl aliquots of the peptide at different concentrations (three assays for each) were added to the cultures, allowing the minimum inhibition concentration (MIC) to be measured. The plate was then further incubated overnight (~16 hours) at 37° C. and read on an Ultra Microplate Reader at 620 nm (Bio-TEK Instruments).

Analytical reverse-phase HPLC. The retention time of each peptide was measured on an ISCO HPLC system equipped with a Vydac C18 reverse-phase column (250×4.6 mm). The peptide was eluted with a linear gradient of acetonitrile (containing 0.1% TFA) from 5% to 95% at a flow rate of 1 ml/min. Peptides were detected by UV absorbance at 215 nm.

NMR spectroscopy. The peptide concentration was ~2 mM in 0.6 ml of aqueous solution of 90% $H_2O$/10% $D_2O$. The pH of each sample was adjusted by using microliter aliquots of HCl or NaOH solution and measured directly in the 5-mm NMR tube with a micro-pH electrode (Wilmad-Labglass). Based on titrations, a peptide/SDS molar ratio of 1:40 and a peptide/D8PG ratio of 1:5 were used.

All NMR data were collected at 25° C. on a Varian INOVA 600 MHz NMR spectrometer equipped with a triple-resonance cold probe with a Z-axis gradient. NOESY spectra were acquired at mixing times of 50 and 100 ms (Jeener et al. (1979) J. Chem. Phys., 71:4546-4553). Additional NOESY spectra at 150 and 200 ms were collected to view the NOE buildup as a function of mixing time. TOCSY experiments were performed with a mixing time of 75 ms using a clean MLEV-17 pulse sequence (Bax et al. (1985) J. Magn. Reson., 65:355-360; Griesinger et al. (1988) J. Am. Chem. Soc., 110:7870-7872). Typically, 2D homonuclear spectra were collected with 512 increments (16-32 scans each) in t1 and 2 K complex points in t2 time domains using a spectral width of 8510.6 Hz in both dimensions with the $^1$H carrier on water. The water signal was suppressed by WATERGATE in the case of NOESY and TOCSY and by low power pre-saturation during relaxation delay for the DQF-COSY experiment (Rance et al. (1983) Biochem. Biophys. Res. Commun., 117: 479-485; Piotto et al. (1992) J. Biomol. NMR, 2:661-665). Natural abundance HSQC spectra (Kay et al. (1992) J. Am. Chem. Soc., 114:10663-10665) involving either $^{15}$N or $^{13}$C were also collected by placing the $^1$H, $^{15}$N, and $^{13}$C carriers at 4.77, 118.27, and 36.37 ppm, respectively. For the $^{15}$N (spectral width 2,200 Hz) and aliphatic $^{13}$C (spectral width 12,000 Hz) dimensions, 30 increments (128 scans) and 80 increments (256 scans) were collected, respectively.

NMR data were processed on a Silicon Graphics Octane workstation (SGI) using the NMRPipe software (Delaglio et al. (1995) J. Biomol. NMR, 6:277-293). The data points in the indirect dimension were doubled by linear prediction for HSQC spectra. Time domain data were apodized by a 63° shifted squared sine-bell window function in both dimensions, zero-filled prior to Fourier transformation to yield a data matrix of 2 K×1 K. To prevent potential interaction of anionic DSS with cationic peptides, the proton chemical shifts of the peptide were referenced to the water signal, which in turn was referenced to internal DSS at 0.00 ppm (Wang et al. (2005) Protein Sci., 12:1087-1096). $^{15}$N and $^{13}$C chemical shifts were referenced based on the ratios recommended by IUPAC (Markley et al. (1998) J. Biomol. NMR, 12:1-23).

NMR data were analyzed with the program PIPP (Garrett et al. (1991) J. Magn. Reson., 95:214-220). The peptide proton signals were assigned using standard procedures based on 2D TOCSY, DQF-COSY, and NOESY spectra (Wuthrich, NMR of Proteins and Nucleic Acids, Wiley, New York, 1986). Natural abundance $^{15}$N, $^{13}$C$^\alpha$, and $^{13}$C$^\beta$ chemical shifts of the micelle-bound peptides were assigned on the basis of the known proton chemical shifts (G. Wang (2006) Curr. Org. Chem., 10:569-581).

Structure calculations. Three-dimensional structures of peptide LLAA in deuterated SDS micelles at pH 4.4 and 25° C. were calculated based on both distance and angle restraints by using the simulated annealing protocol in Xplor-NIH (Schwieters et al. (2003) J. Magn. Reson., 160:65-73). The distance restraints were obtained by classifying the NOE cross-peak volumes into strong (1.8-2.8 Å), medium (1.8-3.8 Å), weak (1.8-5.0 Å), and very weak (1.8-6.0 Å) ranges. The distance was calibrated on the basis of the typical NOE patterns in an α helix (K. Wüthrich, NMR of Proteins and Nucleic Acids, Wiley, New York, 1986). Peptide backbone restraints were obtained from the TALOS analysis of sets of heteronuclear chemical shifts, including $^1$H$^\alpha$, $^{13}$C$^\alpha$, $^{13}$C$^\beta$, and $^{15}$N (Cornilescu et al. (1999) J. Biomol. NMR, 13:289-302). A broader range (±20°) than predicted was allowed for each angle in structural calculations. The side-chain $\chi_1$ angles were derived from a short-mixing-time NOESY spectrum (50 ms) (Clore et al. (1998) Trends Biotechnol., 16:22-34). A covalent peptide structure with random ϕ, ψ, and χ angles but trans planar peptide bonds was used as a starting structure. The peptide structural template was also amidated at the C-terminus. In total, 100 structures were calculated. An ensemble of 20 structures with the lowest total energy was chosen for structural analysis. This final ensemble of accepted structures also satisfies the following criteria: no NOE violations greater than 0.50 Å, rmsd for bond deviations from ideality less than 0.01 Å, and rmsd for angle deviations from ideality less than 5°. The coordinates of the LL-37-derived aurein 1.2 analog have been deposited with the Protein Data Bank (PDB entry 2F3A).

Results

To provide insight into the mechanism of action, three-dimensional structures of antimicrobial peptides in bacterial membranes are helpful. Structural data of antimicrobial peptides (and membrane proteins) are currently obtained in membrane-mimetic models, including organic solvents, detergent micelles, bicelles, lipid vesicles, and lipid bilayers (Wang, G. (2006) Curr. Org. Chem., 10:569-581). While organic solvents are convenient to use, they are only distantly related to the lipid bilayer structure of biological membranes. Lipid vesicles are not convenient for solution NMR studies due to their large size, leading to broad NMR lines. Lipid bilayers are regarded as the best models for solid-state NMR studies. Bicelles (bilayered micelles) are a newer model that has found use in both solution and solid-state NMR studies. The application of bicelles in solution NMR studies, nevertheless, is limited. Detergent micelles have been most widely utilized as a membrane-mimetic model for solution NMR studies. Micelles are relatively simple to make and have favorable tumbling rates in solution. Further, there are deuterated versions of detergents commercially available for both SDS and dodecylphosphocholine (DPC).

Because of the preference of cationic antimicrobial peptides for anionic lipids, PGs have been used as an alternative bacterial membrane-mimetic model (Wang et al. (2003) Protein Sci., 12:1087-1096; Wang et al. (2004) Spectroscopy, 18:257-264; Keifer et al. (2004) Anal. Biochem., 331:33-39; Li et al. (2006) Protein Expr. Purif., 47:498-505; Wang, G. (2006) Curr. Org. Chem., 10:569-581). The choice of PGs stems from the observation that the circular dichroism spectra of the bacterial membrane anchor from the N-terminus of *E. coli* IIA$^{Glc}$ are identical in dioleoylphosphatidylglycerol or a mixture of dioleoylphosphatidylglycerol and dioleoylphosphatidylethanolamine, mimicking the *E. coli* membranes (Wang et al. (2000) J. Biol. Chem., 275:39811-39814). High-resolution NMR spectra were obtained for this peptide in short chain PGs. The peptide was found to adopt a three-turn amphipathic helical structure in short chain PGs (Wang et al. (2005) J. Biol. Chem., 280:5803-5811; Wang et al. (2003) Protein Sci., 12:1087-1096). While the effect of chain length (six to 12) of SDS-like detergents on the helix length of the peptide was evident, PG acyl chain length ranging from six to 10 carbons (longer chain PGs form lipid bilayers) showed little effect, indicating the robustness of short chain PGs. Translational diffusion coefficients of the peptide-lipid complexes reduced with the increase of PG chain length, indicative of an increase in the size of the complex (Wang et al. (2004) Spectroscopy, 18:257-264; Keifer et al. (2004) Anal. Biochem., 331:33-39). Dioctanoylphosphatidylglycerol (D8PG) was chosen in this study because NMR spectra of the peptide in the bound state can be obtained at a lower lipid/peptide molar ratio compared to dihexanoylphosphatidylglycerol (DHPG). At a lower lipid concentration, the interference of strong signals from protonated PGs with the NMR spectra of the peptide is reduced (Wang et al. (2004) Spectroscopy, 18:257-264). In several cases, we have performed parallel NMR studies of the peptides in both short chain PGs and SDS. The 3D structures of those peptides are very similar in the two environments, indicating that SDS mimics short chain PGs well in these particular cases (Wang et al. (2003) Protein Sci., 12:1087-1096; Wang et al. (2004) Spectroscopy, 18:257-264; Keifer et al. (2004) Anal. Biochem., 331:33-39; Li et al. (2006) Protein Expr. Purif., 47:498-505; Wang, G. (2006) Curr. Org. Chem., 10:569-581). As a consequence, deuterated SDS micelles were utilized for optimal structural determination of LLAA and protonated D8PG for investigating peptide-lipid interactions.

FIG. 10 shows a portion of the NOESY spectrum of LLAA bound to SDS micelles. The peptide signals were assigned using standard procedures based on TOCSY, NOESY, and DQFCOSY spectra (K. Wüthrich, NMR of Proteins and Nucleic Acids, Wiley, New York, 1986). Briefly, amino acid spin systems of LLAA were identified in the TOCSY spectrum followed by connecting the amino acids using the NOESY spectrum. Complete assignments of longer side chains were corroborated by the DQF-COSY spectrum.

Figure 11:
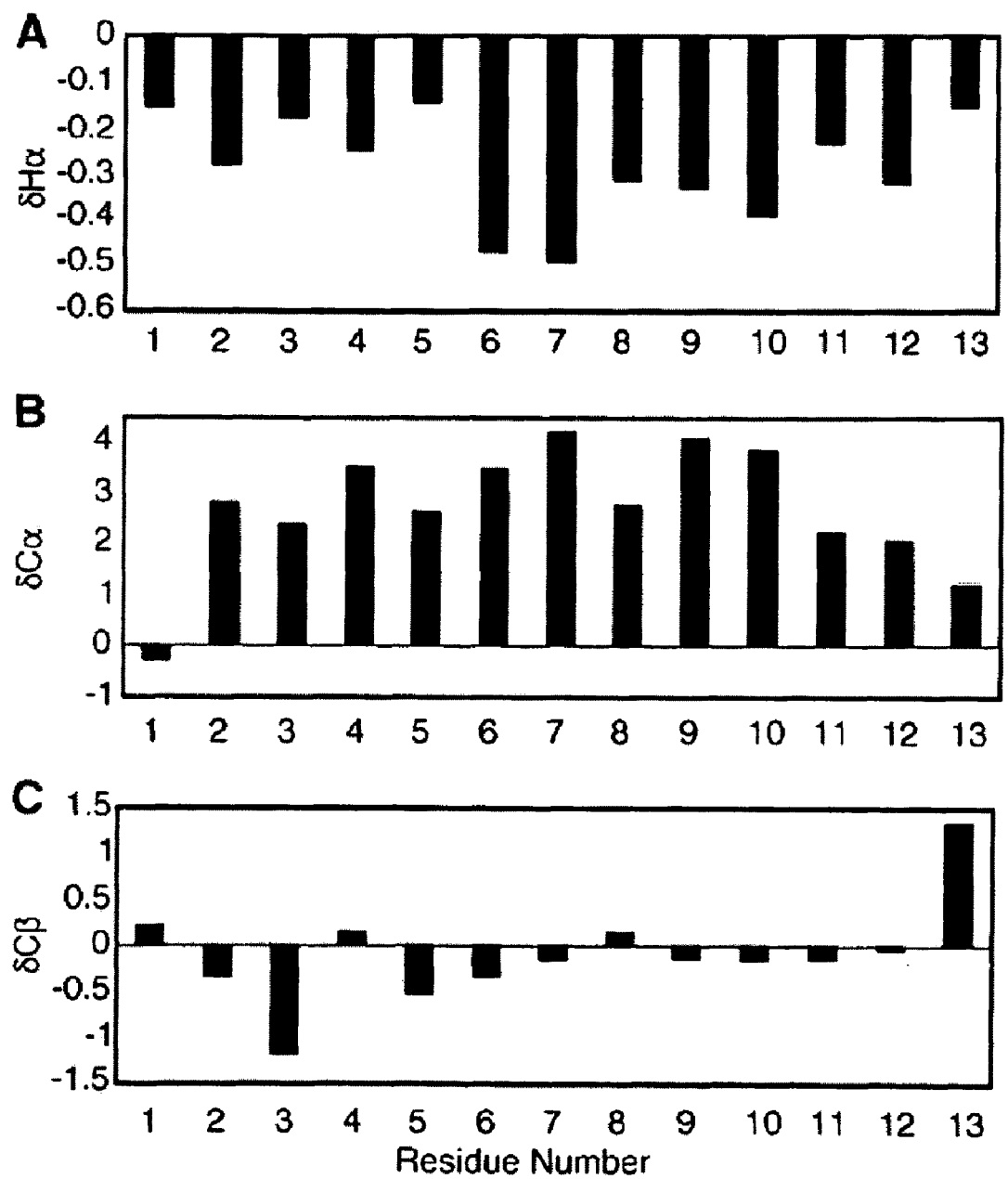

To identify secondary structures in this novel peptide, secondary shifts of α-protons for each residue were calculated (FIG. 11). With heteronuclear chemical shifts available, $^{13}$C secondary shifts were also calculated. Secondary shifts are defined as the chemical shift differences between the measured and the random-coil shifts. A row of negative values (upfield shifts) in the plots for Hα (FIG. 11A) and Cβ (FIG. 11C) and a continued train of positive deviations (downfield shifts) for Cα (FIG. 11B) indicate a helical structure (Wishart et al. (1991) J. Mol. Biol., 222:311-333; Spera et al. (1991) J. Am. Chem. Soc., 113:5490-5492). Therefore, residues 2-12 of LLAA were predicted to be helical. The helicity of the peptide, based on the Hα secondary shifts, is 97% (Table 4). In FIG. 10, (i, i+3) and (i, i+4) types of NOE cross peaks between Hα and amide protons are selectively labeled, indicative of an α-helical structure. Therefore, the secondary structure of LLAA predicted by chemical shifts is in accord with the NOE pattern.

The three-dimensional structure of LLAA was determined based on NOE-derived distance restraints. In total, 191 distance restraints (72 intra-residue, 60 sequential, and 59 short-range) were obtained. Note that the phases of cross peaks for F3, D4, and F13 were slightly influenced by a default water flipback pulse in the Varian 2D wgnoesy pulse sequence. Because these intra-cross-peaks were not included in structural determination, these peaks had no impact on the accuracy of the 3D structures. The structure was further refined using heteronuclear chemical shifts. One approach is to convert these shifts into backbone angles by using TALOS (Cornilescu et al. (1999) J. Biomol. NMR, 13:289-302). An ensemble of 20 structures with the lowest energy was selected by the accept.inp program. A backbone view of the ensemble of LLAA with residues 2-12 superimposed is given in FIG. 12A. The rms deviations for superimposing the backbone, heavy, and all atoms of residues 2-12 of the peptide are 0.19, 0.99, and 1.29 Å, respectively. To further illustrate the quality of the structure, the side chains of the peptide are displayed in FIG. 12B. The hydrophobic side chains (e.g., F3 and F13) superimpose well, indicating good precision. In contrast, the ends of the long cationic side chains such as R1, R7, and R11 are not well superimposed, probably due to both motion and a lack of NOE restraints in those regions. It is clear that the hydrophobic side chains are clustered on one side of the structure (FIG. 12C), while the hydrophilic side chains are located on the opposite side. Consequently, the structure of peptide LLAA is amphipathic. Although TALOS predicted that residues 2-12 are helical, only residues 4-12 of LLAA were found to be helical according to both MOLMOL (Koradi et al. (1996) J. Mol. Graph., 14:51-55) and PROCHECK (Laskowski et al. (1993) J. Appl. Cryst., 26:283-291) analysis of the structural ensemble. The absence of a one-turn helical ribbon at the N-terminus of the peptide might result from the absence of some helical restraints from residue L2 to both K5 and I6 due to spectral overlap (FIG. 10). Nevertheless, 95% of the residues of LLAA are in the most favored region of the Ramachandran plot and 5% are located in the additional allowed region, indicating the overall high quality of the structures.

Figure 13:
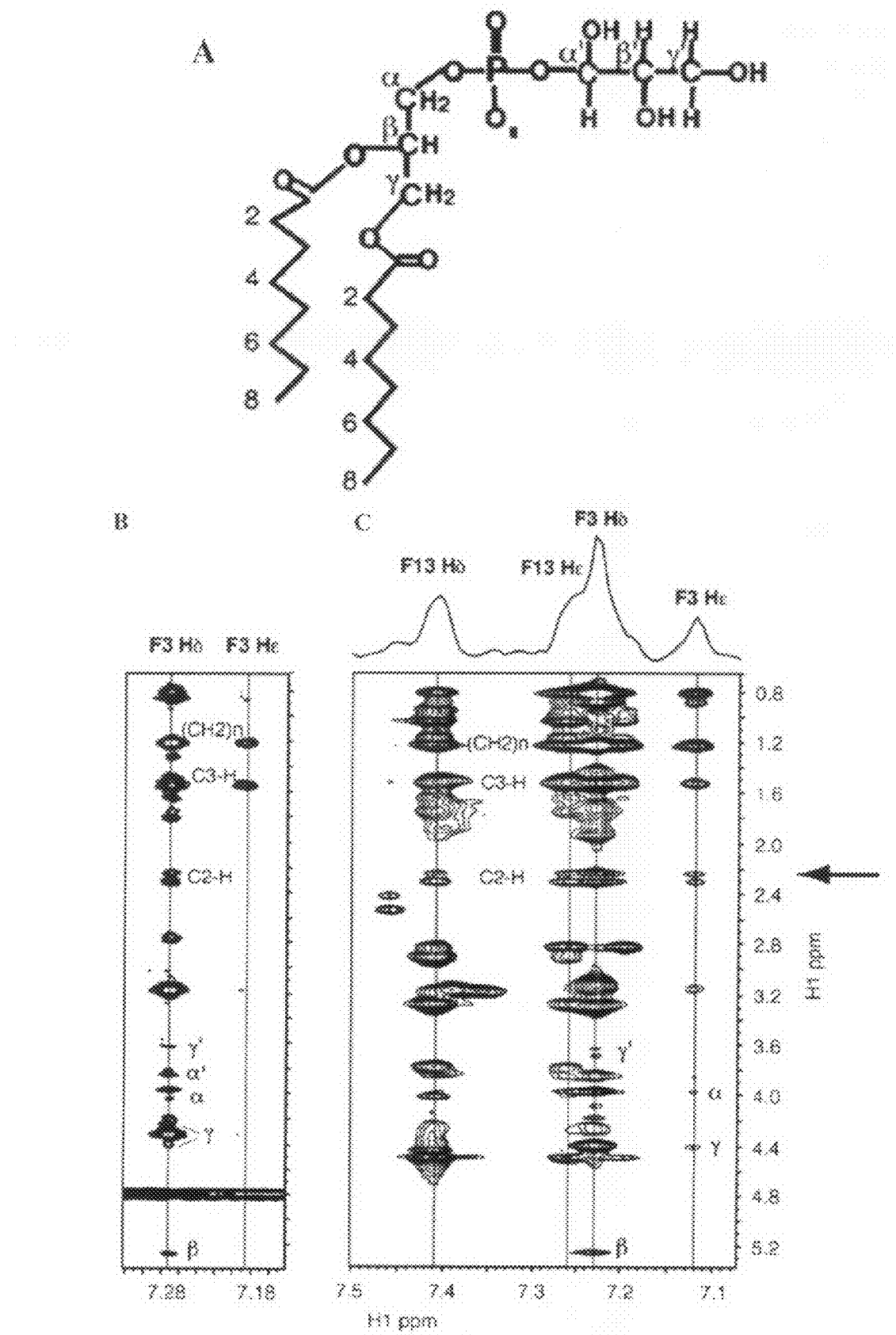

The amphipathic helix of LLAA would be ideal for targeting bacterial membranes. To provide direct evidence for the interaction of this cationic LL-37-derived peptide with anionic lipids, intermolecular NOESY data has also been collected (Wang et al. (2004) Spectroscopy, 18:257-264; Wang et al. (1996) Biochim. Biophys. Acta, 1301:174-184). Since the peptide is not isotopically labeled, relatively well-resolved aromatic resonances were focused on. Of note, the chemical shifts of the aromatic rings of F3 and F13 of LLAA are remarkably similar in SDS and D8PG micelles, indicating their locations in similar chemical environments. FIG. 13 shows the cross peaks between aromatic resonances of LLAA and D8PG. To appreciate these intermolecular NOE cross peaks, FIG. 13A also presents the chemical structure of D8PG with atoms selectively labeled. While both the acyl chains (C2-H, C3-H, (CH$_2$)n, and CH$_3$) and the glycerol portions (α, β, γ) of the lipid interact with F3, there is no NOE cross peak from F13 to the β proton of D8PG (FIG. 13C), suggesting that F13 is immersed more deeply into the lipid micelles than F3. Such an intermolecular NOE pattern for F3 was first observed in the bacterial membrane anchor bound to DHPG (Wang et al. (2003) Protein Sci., 12:1087-1096). Similar results were also observed for this peptide anchor in complex with didecanoyl phosphatidylglycerol (DLOPG) (FIG. 13B). These observations indicate that F3 in either the bacterial membrane anchor or LLAA interacts with lipids in a similar manner.

Because the intensity of NOE cross peaks depends on distance, molecular motion, and mixing time (Clore et al. (1998) Trends Biotechnol., 16:22-34), a qualitative interpretation of intermolecular NOE data is warranted. Using the intermolecular NOE cross peak between aromatic protons and the C2-H of D8PG as an example, normal NOE buildups was observed with an increase in mixing time, confirming that these cross peaks are not derived from spin diffusion. In FIG. 13C, a one-dimensional slice for one of the C2-H of D8PG (indicated by arrow) with the aromatic protons of both F3 and F13 is shown. The NOE intensities of the δ- and ε-protons of F13 with the C2-H of D8PG are more or less the same, indicating that both protons are located approximately at a similar depth in the lipid micelle. However, the intermolecular NOE intensity between the δ-protons of F3 and C2-H protons of D8PG is stronger than that between the ε-protons of F3 and the same C2-H protons, indicating that the aromatic ring of F3 has inserted into the lipid micelles with the ε-proton pointing down as shown in the end-on view of the structure of LLAA. Therefore, the orientations of aromatic rings implied by intermolecular NOE cross peaks are consistent with the structure determined in detergent micelles. The agreement between the intermolecular NOE cross peak patterns and the micelle-bound structure of LLAA further justifies the usefulness of aromatic phenylalanines as a probe (i.e., the F-probe) for membrane penetration of antimicrobial peptides (Wang et al. (2005) J. Biol. Chem., 280:5803-5811). In a model for LLAA in complex with D8PG, both aromatic rings are placed slightly below lipid head groups because the NOE cross peaks to acyl chains are stronger than those to lipid head groups (FIG. 13).

Antibacterial assays revealed that LLAA is more toxic to E. coli than aurein 1.2, which, in turn, is more toxic than the bacterial membrane anchor (Table 1). To explain the activity differences of this series of aurein 1.2 analogs, the 3D structure-based MPP model was used because a single parameter such as the number of positively charged residues, helicity, or hydrophobicity (as measured by HPLC retention time) does not correlate well with the order of antibacterial activity of the peptides in Table 1. According to the MPP model, a positively charged peptide is attracted to the negatively charged membrane surface via electrostatic interaction followed by penetration into the membrane through hydrophobic interaction. The MPP is determined by a combination of hydrophobicity and charges. In the case of our previously studied aurein 1.2 and the bacterial membrane anchor, both peptides contain two cationic side chains in their membrane-targeting helical domains. The difference in their antibacterial activity was ascribed to the narrower and shorter hydrophobic surface of the membrane anchor than aurein 1.2. Indeed, the membrane-binding hydrophobic surface areas of the bacterial membrane anchor and aurein 1.2 are 586.9 and 772.9 Å$^2$ (average values of 20 structures), respectively. Interestingly, the reverse-phase HPLC retention time of the bacterial membrane anchor (29.5 minutes) is shorter than that of aurein 1.2 (43 minutes), indicating that the HPLC retention time of the peptide may be related to the hydrophobic surface for micelle binding. The narrow hydrophobic surface of the cationic membrane anchor may explain its ability to associate with anionic lipids, but not with zwitterionic phosphocholines (Wang et al. (2000) J. Biol. Chem., 275:39811-39814). Because the bacterial membrane anchor is not toxic to E. coli, this peptide may contain the minimal requirement for targeting negatively charged bacterial membranes. The average exposed hydrophobic surface for the ensemble of structures of LLAA is 636.1 Å$^2$, which is only slightly larger than that of the bacterial membrane anchor. Correspondingly, the retention time of peptide LLAA on a reverse-phase HPLC (30.8 minutes) is also only slightly longer than that of the bacterial membrane anchor (29.5 minutes). Both the exposed hydrophobic surface and the HPLC retention time indicate that LLAA possesses the minimal hydrophobic requirement for targeting bacterial membranes. Consequently, the higher antibacterial activity of LLAA than either aurein 1.2 or the bacterial membrane anchor cannot be attributed to the difference in hydrophobicity, but to the additional cationic residues which raised the MPP of the peptide for perturbing negatively charged bacterial membranes.

The original study of aurein 1.2 already pointed to the importance of F13 since changing F13 to isoleucine eliminated the anticancer activity (Rozek et al. (2000) Eur. J. Biochem., 267:5330-5341). It has also been shown that the non-toxic bacterial membrane anchor could be converted to an antimicrobial peptide by changing D13 to F13 (Wang et al. (2000) J. Biol. Chem., 275:39811-39814; Wang et al. (2005) J. Biol. Chem., 280:5803-5811). To better understand the role of F13 in governing the structure and activity of aurein 1.2, additional mutants were designed with more conservative changes. In one of the mutants, only the β-methylene group ($CH_2$) was eliminated from F13 of aurein 1.2; in other words, F13 was changed to phenylglycine (X). Antibacterial assays of this mutant indicated that the methylene deletion caused a reduction in activity (higher MIC in Table 4) relative to aurein 1.2.

To understand the structural basis for the activity change, the F13X mutant was analyzed in SDS micelles by NMR spectroscopy. A combined $^1H$ and $^{15}N$ backbone chemical shift perturbation (Wang et al. (2000) J. Biol. Chem., 275: 16401-16403) of aurein 1.2 as a result of the F13X mutation was performed. Apparently, this mutation caused more than 100-Hz perturbations only to residues 10-13, indicative of a local effect. Indeed, the calculated helicity of the mutant based on Hα chemical shifts is comparable to that of aurein 1.2 (Table 4). Further, there are also NOE cross peaks from the aromatic ring of X13 to the hydrophobic side chains of I9 and A10, indicating a hydrophobic packing similar to that observed for aurein 1.2. However, the Hα proton of A10 shifted from 4.04 ppm in aurein 1.2 to 3.3 ppm in the F13X mutant. This 0.7 ppm shift of the Hα of A10 may be related to the ring current effect of X13 (Wang et al. (1996) Biochemistry, 35:10358-10366). Indeed, both the γ and δ protons of the X13 aromatic ring showed NOE cross peaks of medium intensity with the Hα of A10, indicating a direct location of the aromatic ring underneath the Hα of A10. Thus, the reduced activity of the F13X analog may result from the packing of the aromatic ring of X13 toward the peptide backbone (as evidenced by the ring current effect). This upper location of the X13 ring also caused a decrease in the hydrophobicity of the peptide. The retention time of the F13X mutant on the reverse-phase HPLC column is 38.3 minutes compared to 43 minutes of aurein 1.2 (Table 4). This may explain the reduced activity of the F13X aurein 1.2 mutant.

It is also noteworthy that the Hα proton of X13 appears at 5.2 ppm while that of F13 resonates at 4.49 ppm. Hence, the Hα proton of X13 is well separated from the rest of the α-protons of this helical peptide, which are all above the water at 4.77 ppm. This unique chemical shift of the Hα of phenylglycine in a helical peptide should be useful for resolving ambiguous assignments when there are multiple phenylalanines in a single antimicrobial peptide. Indeed, ~70 antimicrobial peptides in the APD contain three or more phenylalanines in their sequences (Wang et al. (2004) Nucleic Acids Res., 32:D590-D592). To facilitate the use of this phenylalanine analog in future NMR studies, a set of random-coil chemical shifts for phenylglycine (X) using GGXGG (SEQ ID NO: 17) as a peptide template were obtained. The random shift of the Hα of phenylglycine at 5.47 ppm enables the calculation of its secondary shift. For instance, the secondary shift of the Hα of X13 of the F13X mutant is −0.27 ppm, indicative of an upfield shift.

While the F13X mutation caused an upward movement of the C-terminal aromatic ring toward the peptide backbone, F13 was also changed to tryptophan (F13W) so that the six-membered aromatic ring is further away from the peptide backbone than that of F13. Surprisingly, this mutation essentially eliminated the bioactivity of the peptide (MIC=320 μM in Table 4), although the structural perturbation of this mutation is local according to the chemical shift perturbation plot. Therefore, the helical structure of the F13W mutant is retained as also supported by continuous (i, i+3) and (i, i+4) types of NOE cross peaks covering residues 2-13. To provide evidence for the approximation of the aromatic rings to the peptide backbone, the intensity of the NOE cross peak was measured from each aromatic ring to the Hα of A10. To minimize potential intensity differences between the spectra of different peptides, the NOE ratio between the W13 Hε3 (or its equivalent F13 Hδ in aurein 1.2 or X13 Hγ in the F13X mutant)-A10 Hα cross peak and the HN-Hα cross peak of A10 was taken. The ratio involving W13 Hε3 is smallest, followed by F13Hδ, and X13Hγ protons (which is only slightly larger than F13Hδ), indicating that the distance of these aromatic protons to A10 Hα is approximately W13 Hε3>>F13HδN>13 Hγ. In other words, the phenylglycine aromatic ring of the F13X analog is closest to the peptide backbone (also see above, the ring current effect), while the six-membered-ring of the Trp residue of the F13W analog is farthest from the peptide backbone. Therefore, a closer (the F13X mutation) or further (the F13W mutation) location relative to the peptide backbone of the C-terminal aromatic ring of the aurein 1.2 analogs reduces the ability of the peptide to kill bacteria. The sensitivity of the toxicity of aurein 1.2 to the position of the C-terminal aromatic ring (relative to the Hα of A10) further indicates that a proper location of the C-terminal phenylalanine is important for the antibacterial activity of the peptide.

The interactions of the F3 aromatic rings of all these aurein 1.2 analogs with D8PG are more or less similar to those observed for the bacterial membrane anchor (FIG. 13B). For F13 in aurein 1.2, W13 in the F13W analog, and X13 in the F13X analog, the intermolecular NOE cross peaks from these aromatic rings to the C2-H protons of D8PG are much weaker or barely detectable, although there are strong NOE cross peaks to the (CH2)n protons. In contrast, the intermolecular NOE cross peaks from F13 of LLAA to the C2-H of D8PG are clear (FIG. 13C). Therefore, the F13 in aurein 1.2 and the equivalent aromatic rings in its F13 mutants all insert into the lipid micelles more deeply than F13 in LLAA. A deeper penetration of those aromatic rings appears to be related to the higher hydrophobicity of aurein 1.2 and its F13 mutants than LLAA (see the HPLC retention times in Table 4). Since the F13 mutants are not as active as aurein 1.2, it is the proper penetration, rather than a simple deep penetration, that determines the activity of the peptide. It appears to be general in these aurein 1.2 analogs that F13 adopts a slightly deeper location in lipid micelles than F3 (e.g., FIG. 13C). The different locations of the aromatic phenylalanines in the same peptide further support the uniqueness of each aromatic ring in interactions with membranes. Without necessarily being bound by theory, it appears that a proper penetration of the aromatic rings ensures the membrane perturbation potential of an antimicrobial peptide.

Figure 12:
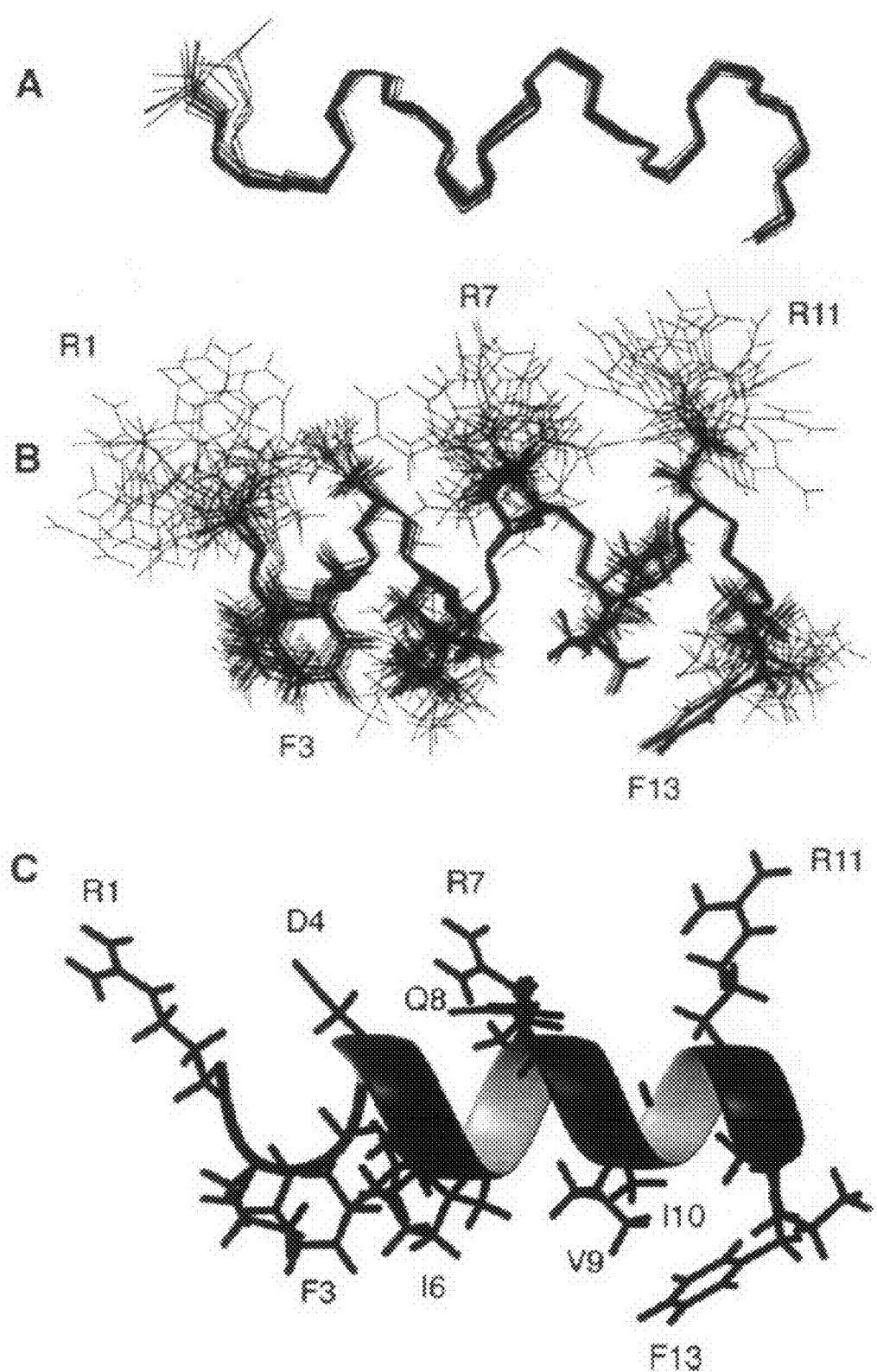

Herein, a novel aurein 1.2 analog from human LL-37 (LLAA) has been identified based on the similarity in the spacing of two aromatic residues. This 13-residue peptide also adopts a helical conformation in membrane-mimetic micelles (FIG. 12). The structural similarity of both bacterial membrane anchor and aurein 1.2 in SDS and short chain PGs micelles adds further confidence in the use of deuterated SDS micelles for the structure determination of LLAA. Actually, the aromatic rings of F3 and F13 of LLAA have nearly identical chemical shifts in SDS micelles or D8PG lipid micelles, indicating the locations of the aromatic rings in a similar environment.

While deuterated SDS micelles facilitate the structural determination of antimicrobial peptides, protonated short chain PGs enable the investigation of peptide-lipid interactions by solution NMR. Indeed, direct evidence for the association of aromatic rings of the LL-37-derived aurein 1.2 analog with D8PG is provided in FIG. 13C. Peptide-lipid intermolecular NOE patterns were also shown to contain information about the penetration depth and orientation of the aromatic rings of phenylalanines in a lipid environment. Interestingly, another solid-state NMR study of a membrane-targeting peptide in a lipid bilayer arrived at a similar conclusion (Zhang et al. (2003) J. Biol. Chem., 278:21459-21466). Accordingly, it appears that the aromatic rings of F3 and F13 of peptide LLAA are located underneath the head groups of D8PG. Similar locations of aromatic rings of phenylalanines observed by magic-angle spinning solid-state NMR in lipid bilayers (Zhang et al. (2003) J. Biol. Chem., 278:21459-21466) and by solution NMR in lipid micelles (Wang et al. (2005) J. Biol. Chem., 280:5803-5811; Wang et al. (2003) Protein Sci., 12:1087-1096) further illustrate the usefulness of short chain PGs in providing insights into peptide-lipid interactions (Wang et al. (2004) Spectroscopy, 18:257-264), even though the membrane-targeting peptides in the two studies differ. It appears that the penetration depth of aromatic phenylalanines is related to their positions in the peptide as well as the peptide hydrophobicity as measured by HPLC. Since ~67% of the antimicrobial peptides in the APD (Wang et al. (2004) Nucleic Acids Res., 32:D590-D592) possesses at least one phenylalanine, this aromatic residue, and perhaps other aromatic residues as well (Wang et al. (1997) Biochemistry, 36:13657-13666), may serve as a useful probe for membrane penetration and binding of membrane-targeting peptides.

The importance of F13 of aurein 1.2 in targeting the bacterial membrane and killing bacteria is further supported by the mutagenesis data provided herein. An alteration of F13 to either phenylglycine or tryptophan reduces the toxicity of the peptide toward *E. coli*. Since the overall helical structure is maintained in these mutants, the activity change may result from different locations of the last aromatic residue (F13, W13 and X13) relative to the peptide backbone. The subtle change from phenylalanine to phenylglycine (viz., only a CH2 group) may be useful as a modulator for peptide design. Further, the unique chemical shifts of phenylglycine (δ(ppm) $H^N$, $^{15}N$ (8.81, 123.64) Hα, $^{13}C\alpha$ (5.47, 61.23); Aromatic: 1H, 7.44; 13C 130.41, 131.96) may be employed as an aid for NMR studies of antimicrobial peptides with multiple phenylalanines.

It is remarkable to find sequence homology among the bacterial membrane anchor, aurein 1.2, and a segment from human LL-37 (Table 4). The membrane anchor of the glucose-specific enzyme IIA of the bacterial phosphotransferase system is essential for the terminal phosphoryl transfer of the *E. coli* signal transduction pathway, while aurein 1.2 is a key antimicrobial peptide from an Australian frog. LL-37 is the only human antimicrobial peptide in the family of cathelicidins and is essential for human defense against infection. Since the bacterial membrane anchor is not toxic to *E. coli*, it serves as a useful control for a good understanding of the activity of aurein 1.2, which became active by increasing its hydrophobicity. In turn, the bacterial membrane anchor and aurein 1.2 set a ladder toward a better understanding of the activity of the LL-37-derived aurein 1.2 analog. Because LLAA is as hydrophobic as the bacterial membrane anchor (Table 1), the higher activity of LLAA than aurein 1.2 is not due to a higher hydrophobicity, but due to an increased number of positively charged residues. Thus, antibacterial activity of an antimicrobial peptide could be augmented by an increase in either hydrophobicity (e.g., from the anchor to aurein 1.2) or cationic residues (e.g., from the anchor to LLAA). Such observations further reinforce the usefulness of the structure-based MPP model, which takes both hydrophobicity and charges into consideration. This work also lays the basis for quantifying the membrane perturbation potential as more data accumulate (Table 4). The discovery of peptide sequences homologous to amphibian antimicrobial peptide aurein 1.2 from bacteria and humans suggests a useful sequence in nature could be utilized by a variety of species for different or similar purposes by interacting with cellular membranes and perhaps other targets as well.

Since sequence reversal had little effect on the activity of the LL-37 core antimicrobial peptide corresponding to residues 17-29, the 3D structure (FIG. 12) as well as the results on peptide-lipid interactions (FIG. 13) should also provide insight into the mechanism of action of human LL-37. Notably, Ramamoorthy and colleagues have investigated the effect of LL-37 on lipid bilayers by $^2$H, $^{31}$P, and $^{15}$N NMR (Henzler-Wildman et al. (2004) Biochemistry 43:8459-8469; Henzler-Wildman et al. (2003) Biochemistry 42:6545-6658). Both $^2$H and $^{31}$P are excellent probes in lipids that offer insight into structure and dynamics of specific lipids as well as the lipid phase. In the presence of LL-37, a decrease in the quadrupolar splitting of $^2$H along the acyl chain was found, indicating increased disorder in lipid chains caused by the peptide (Henzler-Wildman et al. (2004) Biochemistry 43:8459-8469). Further, $^{31}$P NMR indicates that LL-37 also changes the tilt or wobble of lipid head groups. Another advantage of solid-state NMR is its capability of determining the orientation of antimicrobial peptides in lipid bilayers. Using $^{15}$N NMR and site-specific isotope labeling, the putative helical structure of LL-37 was found to be oriented parallel to the membrane surface (Henzler-Wildman et al. (2003) Biochemistry 42:6545-6658). Similar information was obtained by solid-state NMR for several other antimicrobial peptides, including magainin (from frog) and its analog MSI-78, pardaxin from fish, protegrin-1 from pig, and polyphemusin I from horseshoe crab (Bechinger et al. (2005) Biochim. Biophys. Acta, 1712:101-108; Mecke et al. (2005) Biophys. J., 89:4043-4050; Hallock et al. (2002) Biophys. J., 83:1004-1013; Porcelli et al. (2004) J. Biol. Chem., 279:45815-45823; Mani et al. (2005) Biochim. Biophys. Acta, 1716:11-18; Powers et al. (2005) Biochemistry 44:15504-15513). Among them, magainin, MSI-78, and pardaxin form helical structures while protegrin and polyphemusin I form β-hairpin structures (see, e.g., aps.unmc.edu/AP/main.html). In several studies, both solid-state and solution NMR techniques have been utilized. Such a combined use of NMR techniques takes advantage of the efficiency of solution NMR in determining the structure of antimicrobial peptides and the capability of solid-state NMR in providing additional lipid information in lipid bilayers. The unique part of our contribution in this study is both high-quality 3D structure and invaluable direct evidence for peptide-lipid interaction. Because PGs are true lipids, the instant results obtained by solution NMR should be more applicable to lipid bilayers. Of interest is that both F3 (close to the N-terminus of the peptide LLAA) and F13 (at the C-terminus) show clear intermolecular NOE cross peaks with D8PG (FIG. 13), depicting a picture for the first time that the cationic amphipathic helix will be directly located on the membrane surface to interact with anionic PG electrostatically, with the aromatic rings (and other hydrophobic side chains) penetrating into lipid bilayers via hydrophobic interactions, thereby influencing lipid structure and dynamics detectable by solid-state NMR. Thus, a combined use of solid-state and solution NMR is able to provide details on the mechanism of action of antimicrobial peptides at the atomic level.

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated LL-37 peptide having antimicrobial activity and having from 13 to 21 amino acids, wherein the amino acid sequence from positions 1 to 13 of said LL-37 peptide has at least 80% identity with SEQ ID NO: 5, and wherein at least one of the amino acids at positions 4, 8, and 12 is a D-amino acid.

2. The isolated LL-37 peptide of claim 1, wherein the amino acid sequence from positions 1 to 13 of said LL-37 peptide has at least 90% identity with SEQ ID NO: 5.

3. The isolated LL-37 peptide of claim 1, wherein said LL-37 peptide has 13 to 18 amino acids.

4. The isolated LL-37 peptide of claim 1, wherein said LL-37 peptide has at least 80% identity with SEQ ID NO: 4.

5. A pharmaceutical composition comprising at least one LL-37 peptide of claim 1 and at least one pharmaceutically acceptable carrier.

6. A method for treating a bacterial infection in a patient comprising administering the pharmaceutical composition of claim 5 to a patient in need thereof.

7. The isolated LL-37 peptide of claim 1, wherein said peptide comprises D-amino acids spaced by three consecutive L-amino acids.

8. The isolated LL-37 peptide of claim 1, wherein the amino acids at positions 4, 8, and 12 are D-amino acids.

9. The isolated LL-37 peptide of claim 1, wherein said peptide is amidated.

10. The isolated LL-37 peptide of claim 1, wherein said peptide is acetylated.

* * * * *